United States Patent [19]
Alker et al.

[11] Patent Number: 5,089,505
[45] Date of Patent: Feb. 18, 1992

[54] 1-ARYLETHYL-3-SUBSTITUTED PIPERIDINES

[75] Inventors: David Alker, Birchington; Peter E. Cross, Canterbury; Robert M. Wallis, Ramsgate, all of England

[73] Assignee: Pfizer Inc., New York, N.Y.

[21] Appl. No.: 376,263

[22] Filed: Jul. 6, 1989

[30] Foreign Application Priority Data

Jul. 8, 1988 [GB] United Kingdom ............ 8816365

[51] Int. Cl.$^5$ .................. A61K 31/445; A61K 31/55; C07D 405/06; C07D 405/14
[52] U.S. Cl. .................... 514/321; 514/319; 514/320; 514/324; 514/325; 546/196; 546/197; 546/202; 546/204; 546/205
[58] Field of Search ............. 544/360, 364; 546/194, 546/196, 202, 204, 213, 216, 221, 197, 205; 514/252, 253, 255, 318, 320, 324, 326, 327, 319, 321, 325

[56] References Cited

U.S. PATENT DOCUMENTS 2,745,837  5/1956  Papa et al. ............ 546/216
2,974,146  3/1961  Biel ...................... 546/216

FOREIGN PATENT DOCUMENTS 0541598  5/1957  Canada .
688345   3/1953  United Kingdom .
780027   7/1957  United Kingdom .
943603  12/1963  United Kingdom .

Primary Examiner—Mary C. Lee
Assistant Examiner—Lenora A. Miltenberger
Attorney, Agent, or Firm—Peter C. Richardson; Paul H. Ginsburg; Valerie M. Fedowich

[57] ABSTRACT

A series of novel 1-(phenethyl) and 1-(1-heteroarylethyl)-3-substituted piperidine derivatives have been prepared, including their pharmaceutically acceptable salts and various novel key intermediates therefor. The 3-substituent present in these compounds is an unsubstituted or substituted diphenylmethoxy group or a diphenylmethoxy-derived group, while the 1-substituent is unsubstituted or substituted phenethyl or 1-(2-heteroarylethyl) wherein the heteroaryl moiety is thienyl, pyridyl or pyrazinyl. These compounds in the form of both their racemates and 3R-isomers, are useful in therapy as smooth muscle muscarinic receptor antagonists and therefore, are of value in the treatment diseases associated with altered motility and/or smooth muscle tone. The most preferred compound is (3R)-diphenylmethoxy-1-(3,4-methylenedioxyphenethyl)-piperidine. Methods for preparing these compounds from known starting materials are provided.

14 Claims, No Drawings

1-ARYLETHYL-3-SUBSTITUTED PIPERIDINES

BACKGROUND OF THE INVENTION

This invention relates to certain 1,3-disubstituted piperidine derivatives.

More specifically, this invention relates to 1-arylethyl-3-substituted piperidine derivatives as selective muscarinic receptor antagonists.

GB-780,027 discloses, amongst other compounds, 3-(benzhydryloxy)- and 3-(xanthyloxy)-N-aralkyl-piperidines as oxytocic agents, being devoid of antispasmodic activity at the therapeutic doses employed. No N-phenethyl substituted examples were synthesised or exemplified within the scope.

U.S. Pat. No. 2,974,146 provides N-aralkyl-3-piperidyl benzhydryl ethers having activity as sedatives and in prolonging the hypnotic effect of barbiturates, with only the corresponding quaternary ammonium salts being stated to possess gastro-intestinal antispasmodic activity. Although N-phenethyl-3-piperidyl benzhydryl ether is listed as "a specific compound provided by the invention", no preparative details or pharmacological data are presented and it is clear that the compound was never actually made.

SUMMARY OF THE INVENTION

It has now unexpectedly been discovered that the 1-(phenethyl) and 1-(2-heteroarylethyl)-3-substituted piperidine derivatives provided by the present invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

According to the invention there are provided the 3R,S-(racemic) and 3R-(optically active) forms of the compounds of the formula:

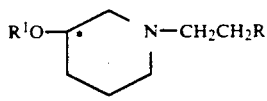

(I)

\* = asymmetric centre and their pharmaceutically acceptable salts, wherein $R^1$ is a group of the formula:

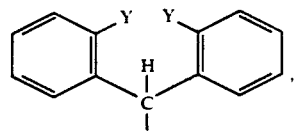

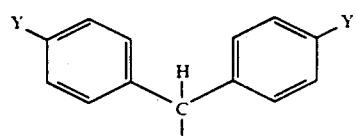

or

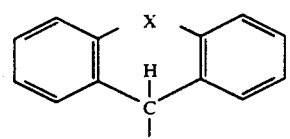

where each Y, which may be the same or different, is selected from the substituents hydrogen, halo and $C_1$-$C_4$ alkyl; tX is —(CH$_2$)$_2$—, —CH=CH—, —CH$_2$—S—, —CH$_2$—O—, —S— or —O—; and R is a group of the formula:

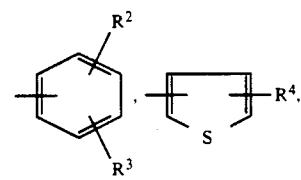

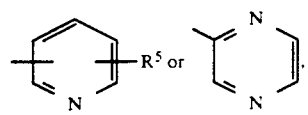

where
either $R^2$ and $R^3$ are each independently hydrogen, $C_1$-$C_4$ alkyl, hydroxy-($C_1$-$C_4$ alkyl), hydroxy, $C_1$-$C_4$ alkoxy, halo, trifluoromethyl, nitro, cyano, sulphamoyl, —CO($C_1$-$C_4$ alkyl), —OCO($C_1$-$C_4$ alkyl), —CO$_2$($C_1$-$C_4$ alkyl), —(CH$_2$)$_n$CONR$^6$R$^7$, —(CH$_2$)$_n$OCONR$^6$R$^7$, —(CH$_2$)$_n$NR$^8$R$^9$ or —NHSO$_2$NH$_2$ in which $R^6$ and $R^7$ are each independently H or $C_1$-$C_4$ alkyl, n is 0, 1 or 2, and either $R^8$ and $R^9$ are each independently H or $C_1$-$C_4$ alkyl or $R^8$ is hydrogen and $R^9$ is —SO$_2$($C_1$-$C_4$ alkyl), —CO($C_1$-$C_4$ alkyl) or —CONH($C_1$-$C_4$ alkyl);

or $R^2$ and $R^3$ taken together, and when attached to adjacent carbon atoms, represent a group of the formula —O(CH$_2$)$_m$O— where m is 1, 2 or 3, —O(CH$_2$)$_2$— or —(CH$_2$)$_3$—;

$R^4$ is H, $C_1$-$C_4$ alkyl or —CONH$_2$;

and $R^5$ is H, $C_1$-$C_4$ alkyl or $C_1$-$C_4$ alkoxy.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

Preferred groups for $R^1$ include:

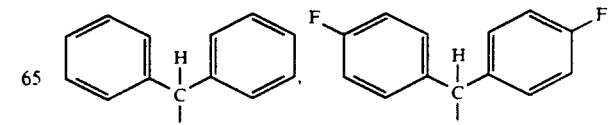

-continued

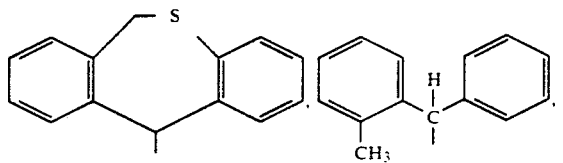

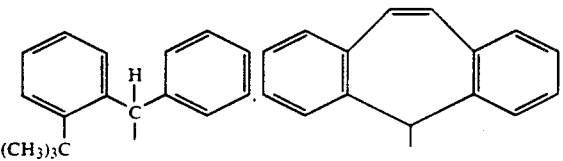

and

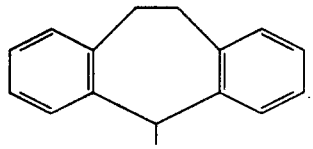

In one aspect, each Y is preferably the same.
When R is an optionally substituted phenyl group, then it preferably has the formula:

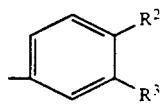

where $R^2$ and $R^3$ are as defined for formula (I).

When R is an optionally substituted thiophene group, it preferably has the formula:

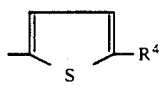

where $R^4$ is as defined for formula (I).
Preferred groups for R include the following:

(a) 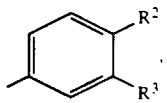

where either $R^2$ and $R^3$ are each independently hydrogen, $C_1$-$C_2$ alkyl, hydroxy-($C_1$-$C_3$ alkyl), hydroxy, $C_1$-$C_2$ alkoxy, halo, sulphamoyl, —CO($C_1$-$C_2$ alkyl), —OCO($C_1$-$C_2$ alkyl), —CONH$_2$, —CONH($C_1$-$C_2$ alkyl), —OCONH($C_1$-$C_2$ alkyl), —NH$_2$, —CH$_2$NH$_2$, —CH$_2$NH($C_1$-$C_2$ alkyl), —NHSO$_2$($C_1$-$C_2$ alkyl), —NHCO($C_1$-$C_2$ alkyl), —CH$_2$NHCO($C_1$-$C_2$ alkyl), —CH$_2$NHCONH($C_1$-$C_2$ alkyl) or —NHSO$_2$NH$_2$; or $R^2$ and $R^3$ taken together represent —O(CH$_2$)$_m$O— where m is 1, 2 or 3, —O(CH$_2$)$_2$—, or —(CH$_2$)$_3$—;

(b)  where $R^4$ is H or —CONH$_2$;

(c) 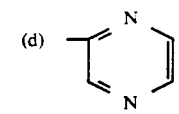 ; or (d) 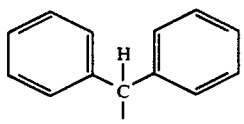

$R^1$ is most preferably:

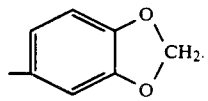

R is most preferably:

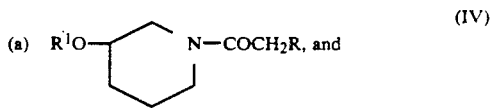

The compounds of the formula (I) contain at least one asymmetric centre and will therefore exist as a pair of enantiomers or as diastereomeric pairs of enantiomers. Such enantiomers or diastereomeric pairs of enantiomers may be resolved by physical methods, e.g. by fractional recrystallisation, chromatography or H.P.L.C. of a racemic mixture of the compound of the formula (I), or of a suitable salt or derivative thereof. Most preferably, the individual enantiomers of the compounds of the formula (I) containing one asymmetric centre are prepared from optically pure intermediates.

The anticholinergic activity of the present compounds resides primarily in the 3R-forms, i.e., the compounds having R stereochemistry at position 3 of the piperidine ring, hence the invention is restricted to the 3R- and 3R,S-(racemic) forms of the compounds (I).

A particularly preferred individual compound of the invention is (3R)-diphenylmethoxy-1-(3,4-methylenedioxyphenethyl)piperidine of a pharmaceutically acceptable salt thereof.

The invention also includes certain synthetic intermediates, namely the 3R,S- and 3R-forms of the compounds of the following formulae:

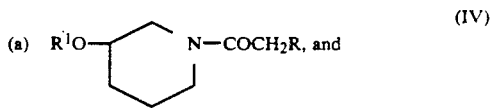

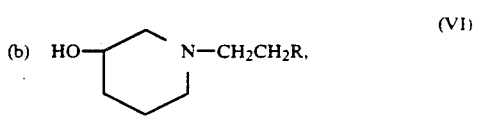

R and $R^1$ being as defined for formula (I).

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

The compounds of the formula (I) can be prepared by a number of routes, including the following:

DETAILED DESCRIPTION OF THE INVENTION

Route A

This can be illustrated as follows:

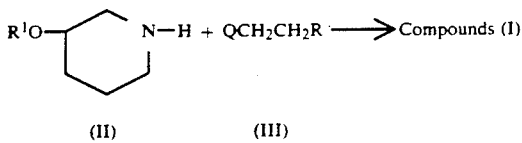

R and $R^1$ are as defined for formula (I) and Q is a leaving group, e.g. Br, Cl, I, $C_1$-$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, sodium bicarbonate, triethylamine or pyridine, and in a suitable organic solvent, e.g. acetonitrile, at up to the reflux temperature. Reaction temperatures of 60°-120° C. are generally desirable and it is most convenient to carry out the reaction under reflux. Iodo is generally the most suitable leaving group but since the starting materials (III) are generally most conveniently available as chlorides or bromides, the reaction is often most suitably carried out using the compound (III) as a chloride or bromide but in the presence of an iodide such as sodium or potassium iodide. In the preferred technique, the compounds (II) and (III), (III) being in bromide or chloride form, are refluxed together in acetonitrile in the presence of sodium carbonate and sodium iodide. The product (I) can be isolated and purified conventionally.

The 3R,S- or 3R-forms of the starting material (II) should be used according to whether the 3R,S- or 3R- products are desired.

The starting materials of the formula (II) can be obtained by conventional procedures such as those described in Preparations 1 to 7. The starting materials of the formula (III) are in general known compounds which can be prepared by conventional techniques. The preparation of the novel starting materials of the formula (III) used in the Examples is described in the following Preparations section.

Route B

This route can be illustrated as follows:

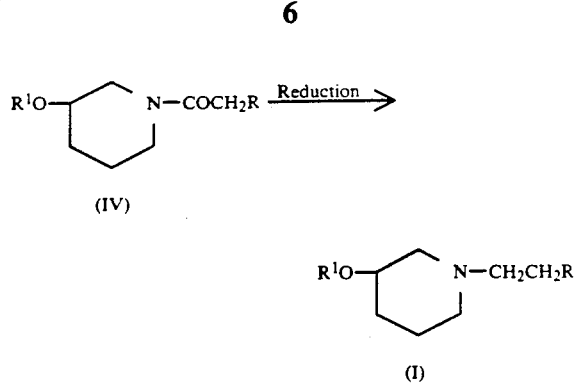

R and $R^1$ are as defined for formula (I): again the 3R,S- or 3R-form of the compound (IV) should be used as appropriate.

The reduction can be carried out conventionally, typically by using an inorganic reducing agent such as lithium aluminium hydride, aluminium hydride (AlH$_3$—made in situ from lithium aluminium hydride and concentrated sulfuric acid) or diborane in a suitable organic solvent such as tetrahydrofuran, ether or dioxane. The reaction is preferably carried out at from 0° C. to room temperature. Heating is generally not needed although, if required, the reaction can be carried out at up to the reflux temperature of the reaction mixture. Again the product (I) can be isolated and purified conventionally.

The starting materials (3R,S- or 3R-) of the formula (IV) can be prepared by conventional techniques including those which are described in the following Preparations (see particularly Preparations 8 to 14).

Route C

This route can be illustrated as follows:

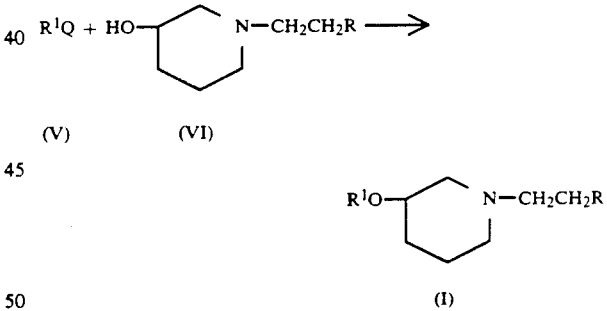

R and $R^1$ are as defined for formula (I) and Q is a leaving group such as described in Route A. In this route, Q is preferably Cl or Br. Where the compound (V) is fairly reactive, then the reaction will proceed to completion at room temperature. If necessary, the reaction mixture can be heated at up to, say, 160° C., to accelerate the rate of reaction. The reaction can be carried in a suitable organic solvent, e.g. methylene chloride, although in some instances, as in Example 8(B), the presence of a separate organic solvent is unnecessary. The compound (I) can be isolated and purified conventionally.

The starting materials (V) are either known compounds or can be prepared conventionally. The compounds (VI) can be prepared conventionally, e.g. by the techniques described in Preparations 15 and 16. Again the 3R,S- or 3R-form of the starting material (VI)

should be used according to whether the 3R,S- or 3R-form of the compound (I) is desired.

Route D

This route is useful for preparing compounds in which R is 2-or 4-pyridyl or pyrazinyl and can be described as follows:

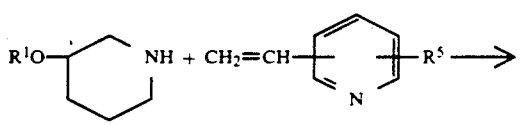

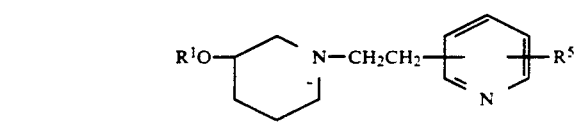

or

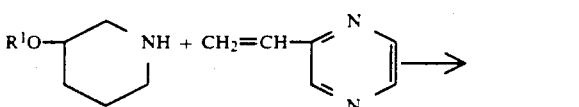

$R^1$ and $R^5$ are as defined for formula (I). Clearly the vinyl group must be attached to the 2- or 4-position of the pyridine ring.

The reaction is typically carried out with heating at up to 160° C., preferably 80° to 140° C., in a suitable organic solvent, e.g. 1-butanol. The use of a basic (preferably a strong base which is soluble in an organic solvent such as N-benzyltrimethylammonium hydroxide ["Triton B"—Trade Mark]) or acidic (preferably a $C_1$-$C_4$ alkanoic acid) catalyst is useful. The preferred procedure is to reflux the reactants in the organic solvent in the presence of a basic catalyst such as "Triton B".

Route E

Compounds in which R is 5-carbamoyl-2-thienyl can also be made by the following route:

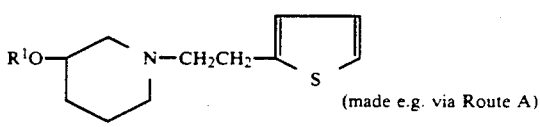

(made e.g. via Route A)

(i) Strong base, e.g. n-BuLi
(ii) $CO_2$

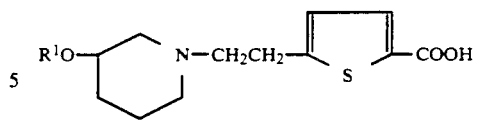

(iii) Formation of an "activated ester" or an imidazolide derivative, e.g. using 1,1'-carbonyldiimidazole
(iv) $NH_3$

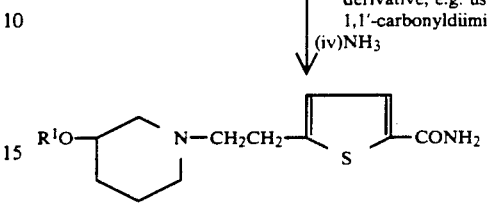

$R^1$ is as defined for formula (I).

Some of the compounds of the formula (I) in which R is a substituted phenyl group can be converted to other compounds of the formula (I) as follows:

(a) A —$CO_2$($C_1$-$C_4$ alkyl) substituent on the phenyl group can be reduced to —$CH_2OH$. Lithium aluminium hydride is the most suitable reducing agent. The reaction is typically carried in a suitable organic solvent, e.g. ether, at between 0° and room temperature. It is generally most convenient to use the starting material in the form of its methyl ester.

(b) A hydroxy substituent on the phenyl group can be converted to —OCO($C_1$-$C_4$ alkyl) by acylation using a $C_1$-$C_4$ alkanoyl chloride or bromide or a $C_1$-$C_4$ alkanoic anhydride. The presence of an acid acceptor is preferable. The reaction is typically carried out at about room temperature in a suitable organic solvent, e.g. dioxan.

(c) A —CO($C_1$-$C_3$ alkyl) substituent on the phenyl group can be reduced to a substituent of the formula —CH(OH)($C_1$-$C_3$ alkyl). Suitable reducing agents include sodium borohydride and lithium aluminium hydride. The reaction is typically carried out at between 0° and room temperature in a suitable organic solvent, e.g. methanol. Sodium borohydride is the preferred reducing agent.

(d) A —$CO_2$($C_1$-$C_4$ alkyl) substituent, preferably —$CO_2CH_3$, can be converted to —$CONR^6R^7$ by reaction with ammonia or the appropriate amine $R^6R^7NH$. When $R^6$ and $R^7$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60° to 100° C., is generally necessary. For volatile amines, the reaction is best carried out in a bomb.

(e) A nitro substituent on the phenyl group can be reduced to amino by conventional means. The preferred reducing agent is stannous chloride dihydrate and the reaction is typically carried out in an organic solvent such as ethanol under reflux.

(f) An amino substituent on the phenyl group can be converted to —$NHSO_2$($C_1$-$C_4$ alkyl) by reaction with a $C_1$-$C_4$ alkanesulphonyl chloride or bromide or $C_1$-$C_4$ alkanesulphonic anhydride. The presence of an acid acceptor such as pyridine, triethylamine, sodium bicarbonate or sodium or potassium carbonate, is preferable.

It is often most convenient, particularly when a sulphonyl chloride is used, to carry out the reaction in pyridine, the pyridine functioning as both the solvent and the acid acceptor. Heating is not usually necessary: normally the reaction will proceed at a satisfactory rate at room temperature.

(g) A substituent of the formula —$(CH_2)_nNH_2$ where n is 0, 1 or 2 can be converted to —$(CH_2)_nNHCO(C_1-C_4$ alkyl) by reaction with a $C_1-C_4$ alkanoyl chloride or bromide or $C_1-C_4$ alkanoic anhydride. The reaction can be carried out similarly to (f) above. The use of acetic anhydride in ethyl acetate/water with sodium bicarbonate as the acid acceptor is a preferred reaction.

(h) An amino substituent on the phenyl group can also be converted to sulphamoyl by reaction with sulphamide, typically under reflux in an organic solvent such as dioxan.

(i) A hydroxy substituent can be converted to $C_1-C_4$ alkoxy firstly by reaction with a strong base such as sodium hydride, and then by reaction with a $C_1-C_4$ alkyl iodide. The reaction is preferably carried out at about room temperature in a solvent such as dimethylformamide.

(j) A hydroxy substituent of the formula —$(CH_2)_nOH$ where n is 0, 1 or 2 can be converted to —$(CH_2)_nOCONH(C_1-C_4$ alkyl) by reaction with a $C_1-C_4$ alkyl isocyanate. The reaction is typically carried out at about room temperature in a solvent such as methylene chloride.

(k) A hydroxymethyl substituent on the phenyl group can be converted to —$CH_2NR^8R^9$ where $R^8$ and $R^9$ are each independently H or $C_1-C_4$ alkyl by reaction firstly with thionyl chloride and secondly with ammonia or the appropriate amine $R^8R^9NH$. The reaction with thionyl chloride is typically carried out with heating, preferably under reflux, in a solvent such as methylene chloride. The reaction with ammonia or the amine is typically carried out at about room temperature in a solvent such as ethanol.

(l) An acetyl substituent can be converted to —$C(OH)(CH_3)_2$ by reaction with methyllithium, methylmagnesium bromide, methylmagnesium iodide or methylmagnesium chloride. The reaction is typically carried out in a solvent such as ether at a temperature of from 0° C. to room temperature.

(m) An iodo substituent can be converted to $C_1-C_4$ alkoxycarbonyl by reaction, typically at about room temperature, with carbon monoxide in a $C_1-C_4$ alkanol containing a base [e.g. potassium carbonate] and a palladium (II) catalyst [e.g. bis(triphenylphosphine)palladium (II) chloride].

(n) A cyano substituent on the phenyl group can be reduced to aminomethyl, typically by catalytic hydrogenation, e.g. using $H_2$/Pd/C in ethanol containing a small amount of concentrated hydrochloric acid.

(o) A substituent of the formula —$(CH_2)_nNH_2$ where n is 0, 1 or 2 can be converted to a substituent of the formula —$(CH_2)_nNHCONH(C_1-C_4$ alkyl) by reaction with a $C_1-C_4$ alkyl isocyanate. The reaction is typically carried out at about room temperature in a solvent such as methylene chloride. And (p) A $C_1-C_4$ alkoxy substituent, preferably methoxy, can be converted to hydroxy by treatment with a $C_1-C_4$ alkanethiol in the presence of a strong base, e.g. sodium hydride. The reaction is typically carried out by refluxing the reactants in a suitable solvent, e.g. dimethylformamide. Butanethiol is the preferred thiol.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined ($pA_2$ value—Arunlakshana and Schild (1959, Brit. J. Pharmacol., 14, 48-58). Using the above analytical techniques, tissue selectivity for muscarinic receptor antagonists is determined.

Activity against agonist induced bronchoconstriction, gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intraveous or intraperitoneal administration. Thus, the dose to cause a doubling of pupil size is determined as well as the dose to inhibit by 50% the salivation and tremor responses to intravenous oxotremorine.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The following Examples, in which all temperatures are in °C., illustrate the invention:

EXAMPLE 1

(3R,S)-Diphenylmethoxy-1-(3,4-methylenedioxyphenethyl)piperidine

Method A

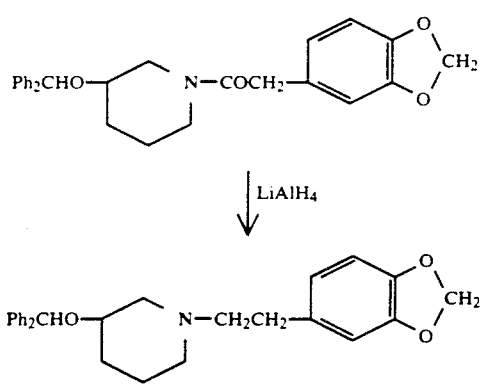

A solution of (3R,S)-diphenylmethoxy-1-(3,4-methylenedioxyphenylacetyl)piperidine (1.08 g) (see Preparation 8) in tetrahydrofuran (10 ml) was added dropwise over 10 minutes to a stirred, ice-cooled suspension of lithium aluminium hydride (0.20 g) in tetrahydrofuran (15 ml), and the mixture was stirred at room temperature for 3 hours, quenched by the addition of saturated aqueous ammonium chloride solution until a white precipitate formed, and then filtered. The filtrate was evaporated and the residue purified by chromatography on silica using methylene chloride containing 0-5% methanol as the eluant. Appropriate fractions were combined and evaporated to give the desired product as a pale yellow oil (0.54 g, 52%) which contained 0.25 molar equivalents of water.

Analysis %: Found: C, 77.2; H, 7.2; N, 3.3; $C_{27}H_{29}NO_3$; $0.25H_2O$ requires: C, 77.2; H, 7.0; N, 3.3.

Method B:

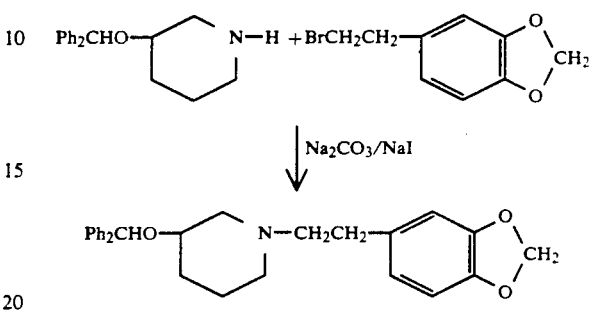

A mixture of (3R,S)-diphenylmethoxypiperidine (2.67 g) (see Preparation 1), 3,4-methylenedioxyphenethyl bromide (2.29 g) (see Preparation 20), sodium carbonate (2.10 g) and sodium iodide (0.25 g) in acetonitrile (50 ml) was heated under reflux for 68 hours, diluted with ethyl acetate and water, and the layers were separated. The organic layer was washed with water, dried over magnesium sulphate and evaporated. The residue was purified by chromatography on silica (50 g) using methylene chloride containing 0-5% methanol as the eluant. Appropriate fractions were combined and evaporated to give the title compound as a pale yellow oil (3.20 g, 77%), whose spectral data was identical with that of the product obtained by Method A.

$^1H$ n.m.r. (CDCl$_3$): $\delta = 7.22$–$7.64$ (10H, m); 7.61–7.80 (3H, m); 5.93 (2H, s); 5.58 (1H, s); 3.52–3.64 (1H, m); 3.13 (1H, dd, J=6 and 2 Hz); 2.54–2.85 (5H, m) and 1.30–2.17 (6H, m).

EXAMPLES 2-7

The following compounds (R,S-forms) were prepared by reduction of the appropriate (3R,S)-starting materials with lithium aluminium hydride as described in Example 1, Method A. All the compounds were obtained as colourless oils and were characterised as such.

Example 2 was characterised by $^1H$-n.m.r.; (CDCl$_3$): $\delta = 7.2$–$7.5$ (10H, m); 6.60–6.88 (3H, m); 5.60 (1H, s); 4.24 (4H, s); 3.52–3.65 (1H, m); 3.09 (1H, d, J=6 Hz); 2.54–2.88 (5H, m) and 1.25–2.15 (6H, m).

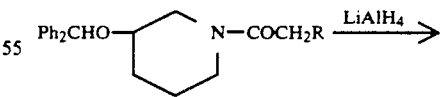

(R, S-form)

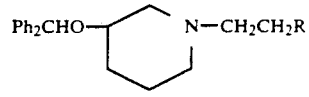

(R, S-form)

The piperidine starting materials are described in Preparations 9-14.

| Example | R | Form Characterised | Analysis % (Theoretical in brackets) | | |
|---|---|---|---|---|---|
| | | | C | H | N |
| 2 | 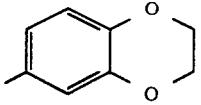 | Free base | Characterised by $^1$H-n.m.r. (vide infra) | | |
| 3 | 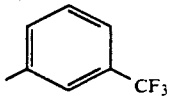 | Free base | 73.4 (73.8 | 6.4 6.4 | 3.1 3.2) |
| 4 | 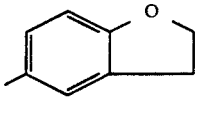 | Free base | 81.3 (81.0 | 7.6 7.5 | 3.4 3.4) |
| 5 | 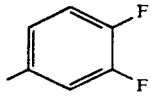 | Free base. 0.25 H$_2$O | 75.4 (75.8 | 6.7 6.7 | 3.7 3.4) |
| 6 | 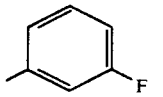 | Free base | 79.8 (80.2 | 7.3 7.2 | 3.5 3.6) |
| 7 | 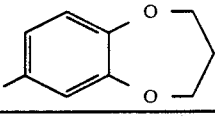 | Free base | 78.2 (78.5 | 7.5 7.5 | 3.2 3.2) |

EXAMPLE 8

(3R,S)-Diphenylmethoxy-1-(3-methoxyphenethyl)-piperidine

Method A

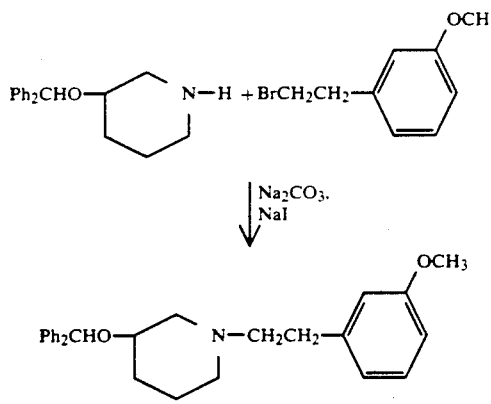

This was prepared as described in Example 1, Method B using 3-methoxyphenethyl bromide instead of 3,4-methylenedioxyphenethyl bromide. The title compound was obtained as a colourless oil (1.37 g, 68%).

Analysis %: Found: C, 80.5; H, 7.8; N, 3.3; C$_{27}$H$_{31}$NO$_2$ requires: C, 80.8; H, 7.8; N, 3.5.

Method B

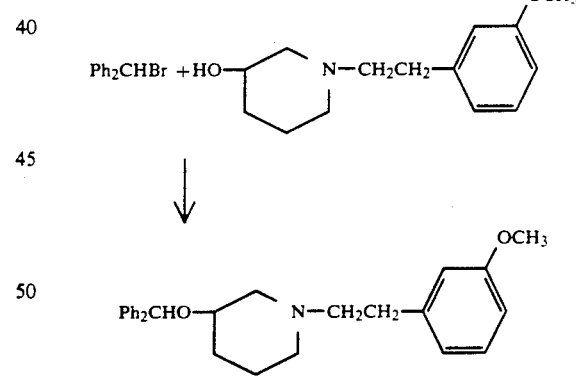

An intimate mixture of (3R,S)-hydroxy-1-(3-methoxyphenethyl)piperidine (1.00 g) (see Preparation 16) and bromodiphenylmethane (0.95 g) was heated at 140° for one hour, allowed to cool to room temperature, dissolved in methylene chloride, washed with 10% aqueous sodium carbonate solution, dried over magnesium sulphate and evaporated. The residue was purified by chromatography on silica (10 g) using methylene chloride as the eluant. Appropriate fractions were combined and evaporated to give the title compound as a colourless oil (0.45 g, 27%) whose spectral data was identical with that of the material obtained by Method A.

$^1$H-n.m.r. (CDCl$_3$): δ=7.14–7.44 (11H, m); 6.72–6.90 (3H, m); 5.59 (1H, s); 3.80 (3H, s); 3.50–3.63 (1H, m);

3.15 (1H, dd, J=6 and 2 Hz); 2.58-2.86 (5H, m) and 1.27-2.16 (8H, m).

EXAMPLES 9-25

The following compounds (R,S-forms) were prepared by reacting (3R,S)-diphenylmethoxypiperidine with the appropriate alkylating agent as described in Example 1, Method B. The alkylating agents are either known compounds or are described in Preparations 24, 25 and 27. All the compounds were obtained as colourless oils and were characterised as such except where indicated.

Examples 17 and 23 were characterised by $^1$H-n.m.r.:

Example 17 (CDCl$_3$): δ=7.99 (2H, d, J=8 Hz); 7.22-7.46 (12H, m); 5.58 (1H, s); 3.96 (3H, s); 3.52-3.62 (1H, m); 3.10 (1H, d, J=6 Hz); 2.60-2.90 (5H, m) and 1.25-2.20 (6H, m).

Example 23 (CDCl$_3$): δ=6.98-7.63 (14H, m); 5.60 (1H, s); 3.52-3.64 (1H, m); 3.10 (1H, d, J=6 Hz); 2.56-2.80 (5H, m) and 1.26-2.18 (6H, m).

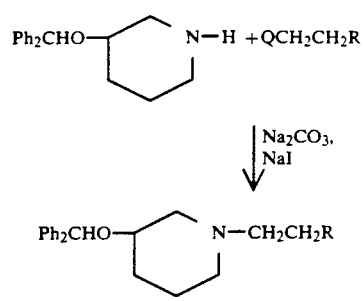

| Example | R | Q | Form Characterised | Analysis (Theoretical in brackets) | | |
|---|---|---|---|---|---|---|
| | | | | C | H | N |
| 9 | ⌬—I (4-I-C$_6$H$_4$) | Cl | Free base, m.p. 108-109° | 63.3 (62.8 | 5.8 5.7 | 2.7 2.8) |
| 10 | ⌬—OMe, OMe (3,4-diOMe) | Cl | Free base | 77.8 (77.9 | 7.8 7.7 | 3.5 3.2) |
| 11 | ⌬—OMe, NO$_2$ | Cl | Free base | 72.6 (72.6 | 6.8 6.8 | 6.5 6.3) |
| 12 | ⌬—NO$_2$ (3-NO$_2$) | Br | Free base | 75.4 (75.0 | 6.9 6.8 | 6.8 6.7) |
| 13 | ⌬—NO$_2$ (4-NO$_2$) | Br | Free base | 74.6 (75.0 | 6.6 6.8 | 7.0 6.7) |
| 14 | ⌬—F | Br | Free base | 80.4 (80.2 | 7.2 7.2 | 3.7 3.6) |
| 15 | ⌬—OH | Br | Free base, 0.25 H$_2$O | 79.7 (79.7 | 7.6 7.6 | 3.6 3.6) |
| 16 | ⌬ (Ph) | Br | Free base | 83.6 (84.0 | 7.5 7.9 | 4.2 3.8) |
| 17 | ⌬—CO$_2$Me | Br | Free base | Characterised by $^1$H-n.m.r. (vide infra) | | |

-continued

| Example | R | Q | Form Characterised | Analysis (Theoretical in brackets) C | H | N |
|---|---|---|---|---|---|---|
| 18 | 4-COMe-phenyl | Br | Free base | 81.2 (81.3) | 7.6 7.6 | 3.2 (3.4) |
| 19 | 4-OH, 3-NO₂-phenyl | Cl | Free base. m.p. 114–115° | 72.0 (72.2) | 6.6 6.5 | 6.4 (6.5) |
| 20 | 4-OH-phenyl | Br | Free base. m.p. 138–140° | 80.1 (80.6) | 7.4 7.5 | 3.6 (3.6) |
| 21 | 2-thienyl | Br | Free base | 75.9 (76.3) | 7.3 7.2 | 4.1 (3.7) |
| 22 | 4-OMe-phenyl | Br | Free base | 80.6 (80.8) | 7.8 7.8 | 3.4 (3.5) |
| 23 | 3-I-phenyl | Br | Free base | Characterised by ¹H-n.m.r. (vide infra) | | |
| 24 | 2-NO₂-phenyl | Br | Free base | 74.9 (75.0) | 6.7 6.8 | 6.6 (6.7) |
| 25 | 2-OCH₃-phenyl | Cl | Free base | 80.7 (80.8) | 7.8 7.8 | 3.5 (3.5) |

EXAMPLE 26

(3R,S)-Di(4-fluorophenyl)methoxy-1-(3,4-methylenedioxyphenethyl)piperidine

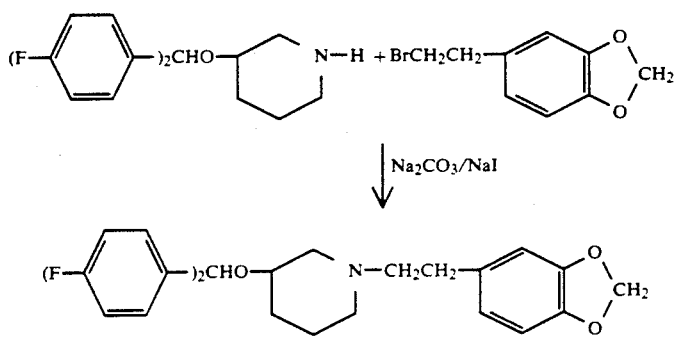

This was prepared as described in Example 1, Method B using (3R,S)-di(4-flourophenyl)methoxypiperidine (see Preparation 2) instead of (3R,S)-diphenylmethoxypiperidine. The title compound was obtained as a colourless oil (0.70 g, 78%).

Analysis %: Found: C, 72.4; H, 6.2; N, 3.0; $C_{27}H_{27}F_2NO_3$ requires: C, 71.8; H, 6.0; N, 3.1.

EXAMPLE 27

1-[2-(Benzodioxan-6-yl)ethyl]-(3R,S)-di(4-fluorophenyl)methoxypiperidine

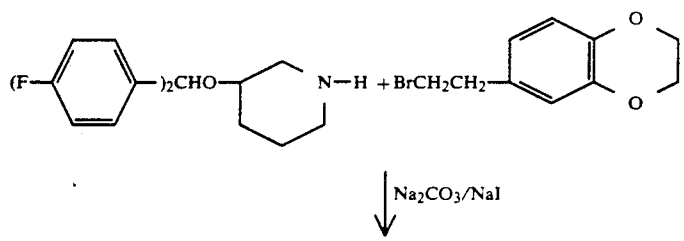

This was prepared by reacting (3R,S)-di(4-fluorophenyl)methoxypiperidine (see Preparation 2) and 6-(2-bromoethyl)benzodioxan (see Preparation 23) according to the procedure described in Example 1, Method B. The title compound was obtained as a colourless oil which was characterised as a hydrate (0.44 g, 51%).

Analysis %: Found: C, 70.0; H, 6.3; N, 2.8; $C_{28}H_{29}F_2NO_3 \cdot H_2O$ requires: C, 69.6; H, 6.4; N, 2.9.

EXAMPLE 28

(3R)-Di(4-fluorophenyl)methoxy-1-(3-methoxyphenethyl)piperidine

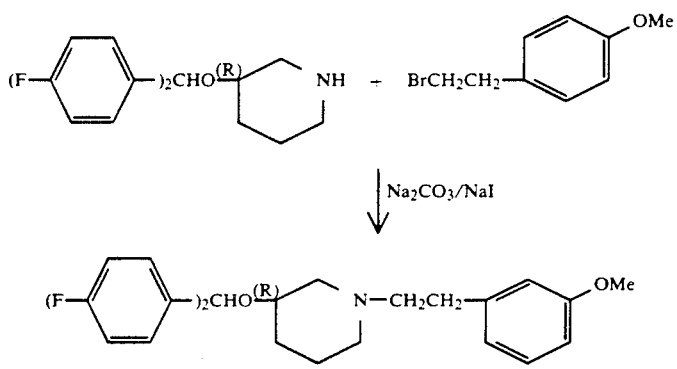

This was prepared by the procedure described in Example 1, Method B from (3R)-di(4-fluorophenyl)methoxypiperidine (see Preparation 3) and 3-methoxyphenethyl bromide. The title compound was obtained as a colourless oil, (0.33 g, 38%).

Analysis %: Found: C, 73.9; H, 6.6; N, 3.1; $C_{27}H_{29}F_2NO_2$ requires: C, 74.1; H, 6.6; N, 3.2.

EXAMPLE 29

(3R)-[(R,S)-1-(2-methylphenyl)-1-phenylmethoxy]-1-(4-methylphenethyl)piperidine

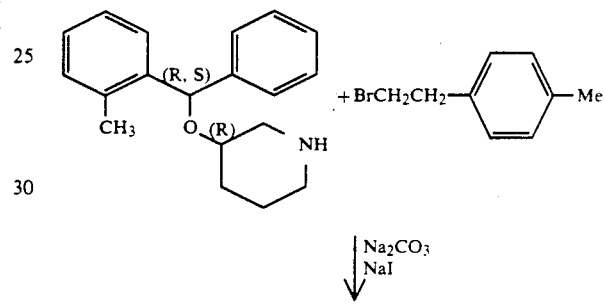

This was prepared by the procedure described in Example 1, Method B from (3R)-[(R,S)-1-(2-methylphenyl)-1-phenylmethoxy]piperidine (see Preparation 4) and 4-methylphenethyl bromide. The title compound was obtained as a pale yellow oil, (0.51 g, 70%), $[\alpha]_D^{14}$ +19.7° (c 1.16 in methanol).

Analysis %: Found: C, 84.1; H, 8.6; N, 3.5; $C_{28}H_{33}NO$ requires: C, 84.2; H, 8.3; N, 3.5.

EXAMPLE 30

(3R)-[1-(2-tert-butylphenyl)-1-phenylmethoxy]-1-(4-methoxyphenethyl)piperidine; Diastereomers A and B

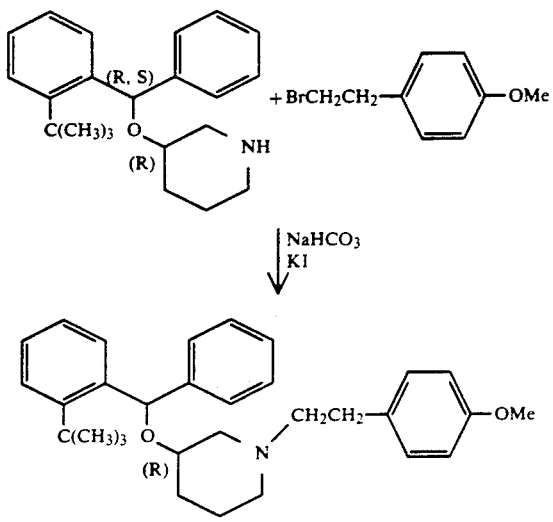

A mixture of (3R)-[(R,S)-1-(2-tert-butylphenyl)-1-phenylmethoxy]piperidine (see Preparation 5) (420 mg), 4-methoxyphenethyl bromide (288 mg), potassium iodide (108 mg) and sodium hydrogen carbonate (169 mg) in acetonitrile (50 ml) was heated under reflux for 16 hours, filtered and evaporated. The residue was purified by chromatography on silica (10 g) using dichloromethane plus 0-4% methanol as eluant. The initial product-containing fractions were combined and evaporated to give the title compound, diastereomer A, as a colourless solid, (300 mg, 50%), m.p. 117° C.

Analysis %: Found: C, 81.3; H, 8.9; N, 2.9; $C_{31}H_{39}NO_2$ requires: C, 81.4; H, 8.6; N, 3.1.

Further elution provided, after combination and evaporation of appropriate fractions, the title compound, diastereomer B, as a colourless solid, (253 mg, 43%), m.p. 108°-113° C.

Analysis %: Found: C, 79.8; H, 8.9; N, 2.7; $C_{31}H_{39}NO_2.0.5H_2O$ requires: C, 79.8; H, 8.6; N, 3.0.

EXAMPLE 31

(3R,S)-[(11H)-6,11-Dihydrodibenzo[b,e]thiepin-11-yloxy]-1-(3-methoxyphenethyl)]piperidine

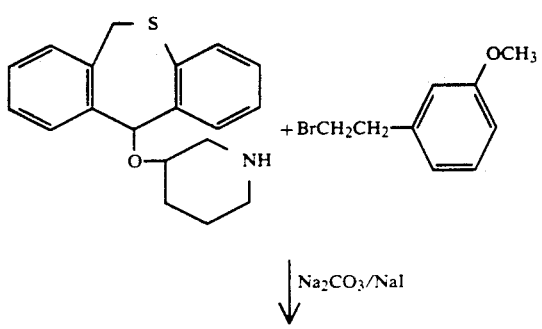

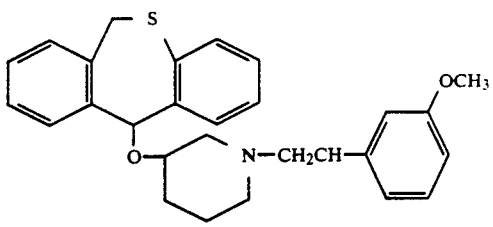

The title compound was prepared by reacting (3R,S)-[(11H)-6,11-dihydrodibenzo[b,e]thiepin-11-yloxy]-piperidine (see Preparation 6) and 3-methoxyphenethyl bromide according to the procedure described in Example 1, Method B. The title compound was obtained as a colourless oil (0.12 g, 11%).

Analysis %: Found: C, 75.4; H, 6.8; N, 2.8; $C_{28}H_{31}NO_2S$ requires: C, 75.5; H, 7.0; N, 3.1.

EXAMPLE 32

(3R)-Diphenylmethoxy-1-(3,4-methylenedioxyphenethyl)piperidine

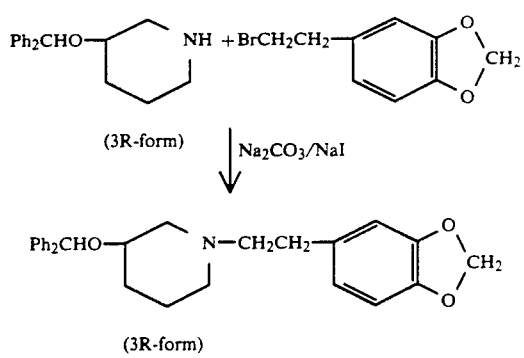

This was prepared as described in Example 1, Method B using (3R)-diphenylmethoxypiperidine $\{[\alpha]_D^{25} -3.3°$ (c 1.5 in ethanol)$\}$ (see Preparation 7) instead of (3R,s)-diphenylmethoxypiperidine. The title compound was obtained as a colourless solid after recrystallisation from hexane (1.25 g, 78%), m.p. 52°-55° C., $[\alpha]^{25} +22.5°$ (c 1.5 in ethanol).

Analysis %: Found: C, 78.4; H, 7.2; N, 3.3; $C_{27}H_{29}NO_3$ requires: C, 78.0; H, 7.0; N, 3.4.

EXAMPLES 33-52

The following compounds (R-forms) were prepared by reacting (3R)-diphenylmethoxypiperidine (see Preparation 7) $[\alpha]_D^{25} -3.0°$ (c 1.5 in ethanol) with the appropriate alkylating agent as described in Example 1, Method B. The alkylating agents are either known compounds or are described in Preparations 21, 23, 29 and 31. The compounds were characterised as the free bases in the forms indicated.

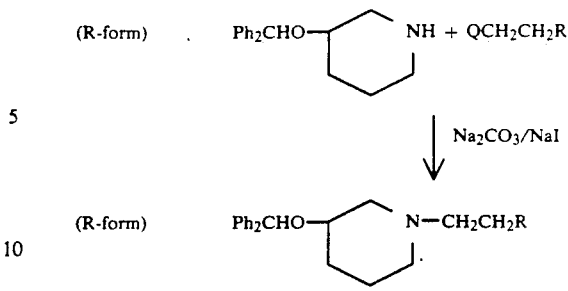

(R-form)  Ph₂CHO—⟨cyclohexane⟩—NH + QCH₂CH₂R

↓ Na₂CO₃/NaI (R-form)  Ph₂CHO—⟨cyclohexane⟩—N—CH₂CH₂R

| Example | R | Q | Form Characterised | Optical Rotation | Analysis % (Theoretical in brackets) C | H | N |
|---|---|---|---|---|---|---|---|
| 33 | ⟨benzodioxane⟩ | Br | oil | [α]$_D^{25}$ + 23.9° (c 1.5 in ethanol) | 78.1 (78.3 | 7.4 7.3 | 3.0 3.3) |
| 34 | ⟨3-OMe-phenyl⟩ | Br | oil | [α]$_D^{25}$ + 20.7° (c 1.5 in ethanol) | 80.1 (80.8 | 7.8 7.8 | 3.5 3.5) |
| 35 | ⟨4-OH-phenyl⟩ | Br | m.p. 156–158° | [α]$_D^{25}$ + 23.8° (c 1.0 in methanol) | 80.2 (80.6 | 7.5 7.5 | 3.4 3.6) |
| 36 | ⟨4-OMe-phenyl⟩ | Br | oil, hemihydrate | [α]$_D^{25}$ + 25.3° (c 1.035 in methanol) | 79.1 (79.0 | 7.7 7.9 | 3.2 3.4) |
| 37 | ⟨4-NHSO₂Me-phenyl⟩ | —OSO₂Me | oil, hemihydrate | [α]$_D^{25}$ + 19.0° (c 1.005 in methanol) | 68.2 (68.5 | 7.2 7.2 | 5.9 5.9) |
| 38 | ⟨4-SO₂NH₂-phenyl⟩ | Cl | m.p. 176–178° | [α]$_D^{25}$ + 20.2° (c 0.87 in methanol) | 69.6 (69.3 | 6.7 6.7 | 6.2 6.2) |
| 39 | ⟨3,4-diOH-phenyl⟩ | Br | m.p. 74–76° | [α]$_D^{25}$ + 22.2° (c 0.98 in methanol) | 76.9 (77.4 | 7.3 7.2 | 3.3 3.5) |
| 40 | ⟨3-OMe-4-OH-phenyl⟩ | Cl | 0.25 H₂O, oil | — | 76.9 (76.8 | 7.6 7.5 | 3.2 3.3) |
| 41 | ⟨4-Me-phenyl⟩ | Br | oil | — | 83.8 (84.1 | 7.9 8.1 | 3.6 3.6) |
| 42 | ⟨4-COCH₃-phenyl⟩ | Cl | oil | — | 81.6 (81.3 | 7.8 7.6 | 2.9 3.4) |

-continued

| Example | R | Q | Form Characterised | Optical Rotation | Analysis % (Theoretical in brackets) | | |
|---|---|---|---|---|---|---|---|
| | | | | | C | H | N |
| 43 | 4-CN-C₆H₄- | Br | oil, hemihydrate | $[\alpha]_D^{25}$ + 19.4° (c 1.025 in methanol) | 80.4 (80.0 | 7.1 7.0 | 6.6 6.9) |
| 44 | 4-CO₂Me-C₆H₄- | Br | m.p. 68-70° | — | 77.7 (78.3 | 7.3 7.3 | 3.0 3.3) |
| 45 | 3-OMe-4-OH-C₆H₃- | Cl | m.p. 118.5-119.5 | $[\alpha]_D^{25}$ + 27.8° (c 1.07 in methanol) | 77.5 (77.7 | 7.6 7.6 | 3.0 3.3) |
| 46 | 4-Cl-C₆H₄- | Br | oil | $[\alpha]_D^{25}$ + 20.4° (c 1.5 in ethanol) | 76.8 (76.9 | 7.0 6.9 | 3.5 3.4) |
| 47 | indanyl | Br | oil | $[\alpha]_D^{25}$ + 24.9° (c 1.5 in ethanol) | 84.5 (84.6 | 7.9 8.1 | 3.4 3.4) |
| 48 | 3,4-Cl₂-C₆H₃- | Br | oil | $[\alpha]_D^{25}$ + 16.7° (c 1.5 in ethanol) | 71.3 (70.9 | 6.3 6.2 | 3.3 3.2) |
| 49 | C₆H₅- | Br | oil, 0.25 hydrate | — | 83.4 (83.1 | 7.7 7.9 | 3.8 3.7) |
| 50 | 3,4-(OMe)₂-C₆H₃- | Br | oil | — | 77.6 (77.8 | 7.7 7.6 | 3.5 3.2) |
| 51 | 2,3-dihydrobenzofuran-5-yl | Br | oil | — | 81.7 (81.4 | 7.6 7.5 | 3.1 3.4) |
| 52 | 3-I-C₆H₄- | Br | oil | — | 64.0 (62.9 | 6.1 5.6 | 3.4 2.8) |

EXAMPLE 53

1-(4-Acetoxyphenethyl)-(3R)-diphenylmethoxypiperidine

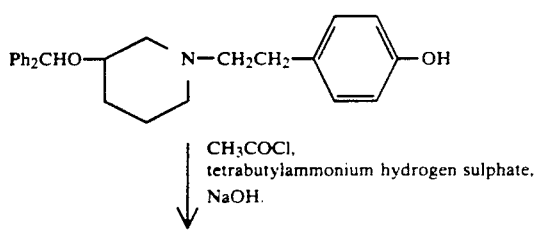

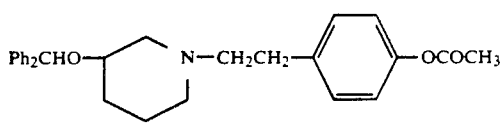

A solution of acetyl chloride (33 ml) in dioxan (5 ml) was added dropwise over thirty minutes to a stirred mixture of (3R)-diphenylmethoxy-1-(4-hydroxyphenethyl)piperidine (150 mg) (see Example 35), tetrabutylammonium hydrogen sulphate (2.7 mg) (a phase transfer catalyst) and powdered sodium hydroxide (50 mg) in dioxan (15 ml) and the mixture was stirred at room temperature for four days, filtered and evaporated. The residue was purified by chromatography on silica (5 g) using methylene chloride plus 0-5% methanol as the eluant. Appropriate fractions were combined and evaporated to give the title compound as a colourless oil (128 mg, 74%), $[\alpha]_D^{25}$ +24.4° (c 0.775 in methanol).

Analysis %: Found: C, 78.3; H, 7.3; N, 3.5; $C_{28}H_{31}NO_3$ requires: C, 78.3; H, 7.3; N, 3.3.

EXAMPLE 54

(3R,S)-Diphenylmethoxy-1-[2-(4-pyridyl)ethyl]piperidine

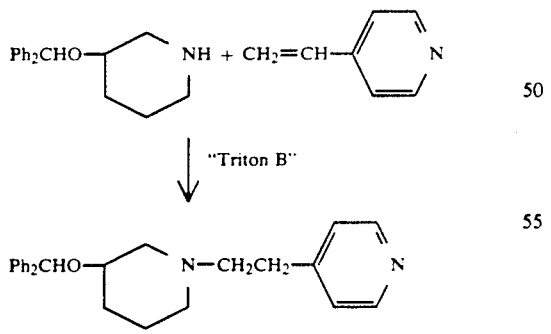

A mixture of (3R,S)-diphenylmethoxypiperidine (534 mg) (see Preparation 1), 4-vinylpyridine (630 mg) and 40% aqueous N-benzyltrimethylammonium hydroxide ("Triton B"—Trade Mark) solution (5 drops) in 1-butanol (20 ml) was heated under reflux for 70 hours and then evaporated. The residue was partitioned between ethyl acetate and water and the organic layer was washed with water, dried over sodium sulphate and evaporated. The residue was purified by chromatography on silica (8 g) using methylene chloride plus 0-5% methanol as the eluant. Appropriate fractions were combined and evaporated to give the title compound as a pale brown gum (310 mg, 42%).

Analysis %: Found: C, 80.3; H, 7.5; N, 7.8; $C_{25}H_{28}N_2O$ requires: C, 80.6; H, 7.6; N, 7.5.

EXAMPLE 55

(3R,S)-Diphenylmethoxy-1-[2-(2-pyridyl)ethyl]piperidine

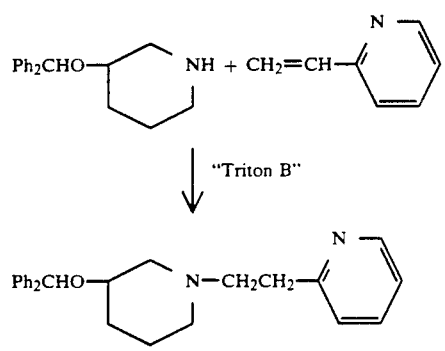

This was prepared as described in Example 54 using 2-vinylpyridine instead of 4-vinylpyridine. The title compound was obtained as a pale brown gum (240 mg, 32%).

Analysis %: Found: C, 80.9; H, 7.6; N, 7.5; $C_{25}H_{28}N_2O$ requires: C, 80.6; H, 7.6; N, 7.5.

EXAMPLE 56

(3R,S)-Diphenylmethoxy-1-[2-(2-pyrazinyl)ethyl]piperidine

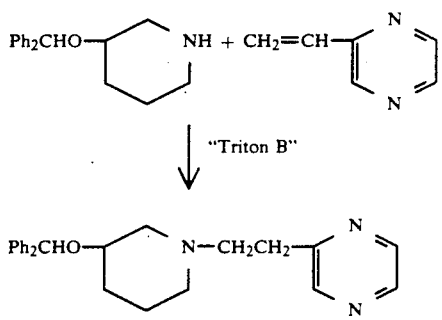

This was prepared as described in Example 54 using 2-vinylpyrazine instead of 4-vinylpyridine. The title compound was obtained as a pale brown gum (185 mg, 50%).

Analysis %: Found: C, 77.2; H, 7.5; N, 11.2; $C_{24}H_{27}N_3O$ requires: C, 77.2; H, 7.3; N, 11.2.

EXAMPLE 57

(3R)-[(5H)-Dibenzo[a,d]cyclohepten-5-yloxy]-1-(4-methoxyphenethyl)piperidine

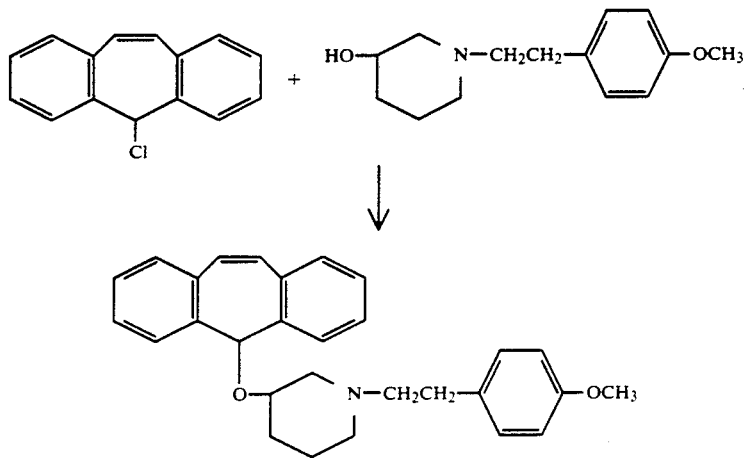

A solution of 5-chloro-(5H)-dibenzo[a,d]cycloheptene (0.49 g), [prepared by chlorination of the commercially available 5-hydroxy compound using thionyl chloride] and (3R)-hydroxy-1-(4-methoxyphenethyl)-piperidine (see Preparation 15) (0.47 g) {$[\alpha]_D^{25}$ −3.0° (c 1.5 in ethanol)} in methylene chloride was stirred at room temperature for four hours, washed with 2M aqueous sodium hydrogen carbonate solution and saturated brine, dried over magnesium sulphate and evaporated. The residue was purified by chromatography on silica (10 g) using methylene chloride plus 0–2% methanol as the eluant. Appropriate fractions were combined and evaporated to give the title compound as a pale orange gum which was characterised as a hemihydrate (300 mg, 35%), $[\alpha]_D^{25}$ +17.4° (c 0.995 in methanol).

Analysis %: Found: C, 79.6; H, 7.2; N, 3.1; $C_{29}H_{31}NO_2$; 0.5H$_2$ requires: C, 80.1; H, 7.4; N, 3.2.

EXAMPLE 58

(3R)-[(5H)-10,11-Dihydrodibenzo[a,d]cyclohepten-5-yl]-1-(4-methoxyphenethyl)piperidine

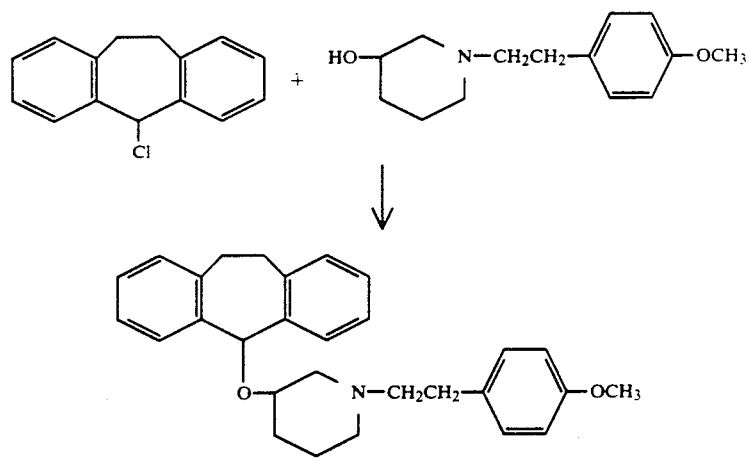

This was prepared as described in Example 57 using 5-chloro-(5H)-10,11-dihydrobenzo[a,d]cycloheptene (commercially available) instead of 5-chloro-(5H)-dibenzo[a,d]cycloheptene. The title compound was obtained as a colourless oil which was characterised as a hemihydrate (491 mg, 58%), $[\alpha]_D^{25}$ +23.8° (c 0.95 in methanol).

Analysis %: Found: C, 79.7; H, 7.6; N, 3.2; $C_{29}H_{33}NO_2$; 0.5H$_2$O requires: C, 79.8; H, 7.8; N, 3.2.

EXAMPLE 59

(3R)-[(11H)-6,11-Dihydrobenzo[b,e]thiepin-11-yloxy]-1-(4-methoxyphenethyl)piperidine

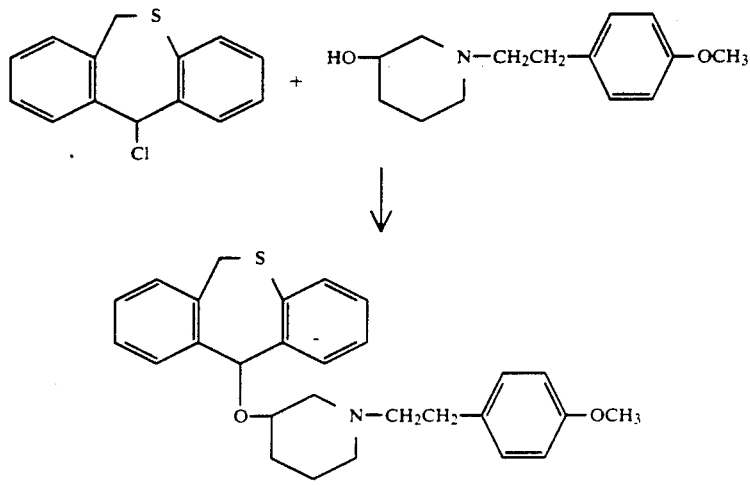

This was prepared as described in Example 57 using 11-chloro-(11H)-6,11-dihydrodibenzo[b,e]thiepine (prepared by the chlorination of the commercially available 11-hydroxy compound using thionyl chloride) instead of 5-chloro-(5H)-dibenzo[a,d]cycloheptene. The title compound was obtained as a colourless oil which was characterised as a hemihydrate (0.80 g, 90%), $[\alpha]_D^{25}$ +18.6° (c 0.81 in methanol).

Analysis %: Found: C, 74.0; H, 7.0; N, 2.9; $C_{28}H_{31}NO_2S$; $0.5H_2O$ requires: C, 74.0; H, 7.1; N, 3.1.

EXAMPLE 60

(3R,S)-Diphenylmethoxy-1-(4-hydroxymethylphenethyl)piperidine

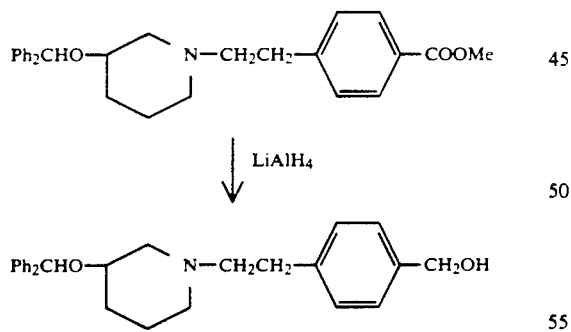

A solution of (3R,S)-diphenylmethoxy-1-(4-methoxycarbonylphenethyl)piperidine (0.43 g) (see Example 17) in ether (5 ml) was added dropwise to a stirred suspension of lithium aluminium hydride (80 mg) in ether (10 ml) and the mixture was stirred at room temperature for four hours, quenched by the sequential addition of water (0.2 ml), 15% aqueous sodium hydroxide solution (0.2 ml) and water (0.6 ml), and filtered. The filtrate was evaporated to give the title compound as a colourless solid (270 mg, 67%), m.p. 93°–95°.

Analysis %: Found: C, 80.2; H, 7.9; N, 3.3; $C_{27}H_{31}NO_2$ requires: C, 80.8; H, 7.7; N, 3.5.

EXAMPLE 61

(3R)-Diphenylmethoxy-1-(4-hydroxymethylphenethyl)piperidine

This was prepared as described in Example 60 using (3R)-diphenylmethoxy-1-(4-methoxycarbonylphenethyl)piperidine (see Example 44) instead of (3R,S)-diphenylmethoxy-1-(4-methoxycarbonylphenethyl)piperidine. The title compound was obtained, after recrystallisation from toluene/60°–80° petroleum ether, as a colourless solid (358 mg, 89%), m.p. 94.5°–95°, $[\alpha]_D^{25}$ +26.3° (c 0.955 in methanol).

Analysis %: Found: C, 80.4; H, 7.8; N, 3.2; $C_{27}H_{31}NO_2$ requires: C, 80.8; H, 7.7; N, 3.5.

EXAMPLE 62

(3R,S)-Diphenylmethoxy-1-[4-(1-hydroxyethyl)phenethyl]piperidine

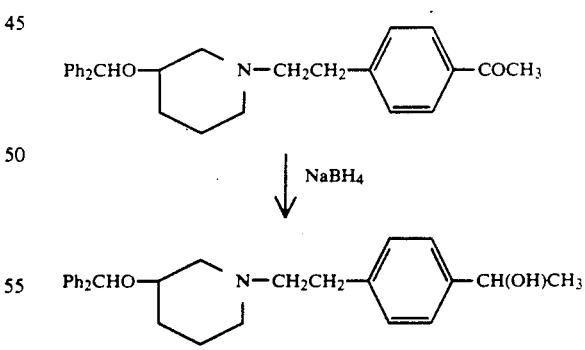

Sodium borohydride (40 mg) was added to a stirred solution of 1-(4-acetylphenethyl)-(3R,S)-diphenylmethoxypiperidine (250 mg) (see Example 18) in methanol (5 ml) and the mixture was stirred at room temperature for fourteen hours, diluted with ethyl acetate, washed twice with water, dried over magnesium sulphate and evaporated to give the title compound as a colourless oil (202 mg, 81%).

Analysis %: Found: C, 80.3; H, 8.1; N, 3.6; $C_{28}H_{33}NO_2$ requires: C, 81.0; H, 7.9; N, 3.4.

EXAMPLE 63

(3R)-Diphenylmethoxy-1-[4-(1-hydroxyethyl)phenethyl]piperidine

This was prepared as described in Example 62 using 1-(4-acetylphenethyl)-(3R)-diphenylmethoxypiperidine (see Example 42) instead of 1-(4-acetylphenethyl)-(3R,S)-diphenylmethoxypiperidine. The title compound was obtained as a yellow oil (131 mg, 33%).

Analysis %: Found: C, 81.2; H, 8.0; N, 3.3; $C_{28}H_{33}NO_2$ requires: C, 81.0; H, 8.0; N, 3.4.

EXAMPLE 64

1-(4-Carbamoylphenethyl)-(3R)-diphenylmethoxypiperidine

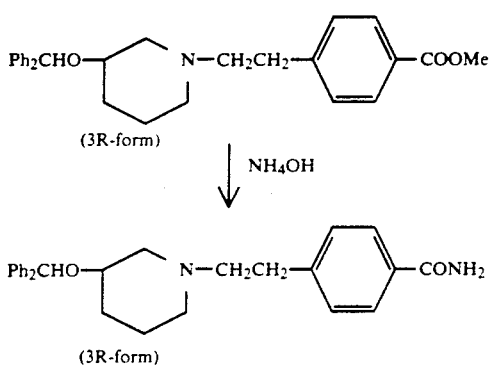

A solution of (3R)-diphenylmethoxy-1-(4-methoxycarbonylphenethyl)piperidine (0.43 g) (see Example 44) in methanol (10 ml) was treated with 0.880 aqueous ammonia (10 ml) and the mixture was heated at 80° for sixteen hours in a steel bomb and then evaporated. The residue was partitioned between ethyl acetate and water and the organic layer was washed with water, dried over magnesium sulphate and evaporated. The residue was purified by chromatography on silica (5 g) using methylene chloride plus 0–5% methanol as the eluant. Appropriate fractions were combined and evaporated to give the title compound as a colourless solid which was characterised as a hemihydrate (75 mg, 16%), m.p. 144.5°–145.5°, $[\alpha]_D^{25}$ +25.1° (c 0.475 in methanol).

Analysis %: Found: C, 76.9; H, 7.4; N, 6.5; $C_{27}H_{30}N_2O_2$; $0.5H_2O$ requires: C, 76.6; H, 7.4; N, 6.6.

EXAMPLE 65

1-(4-Carbamoylphenethyl)-(3R,S)-diphenylmethoxypiperidine

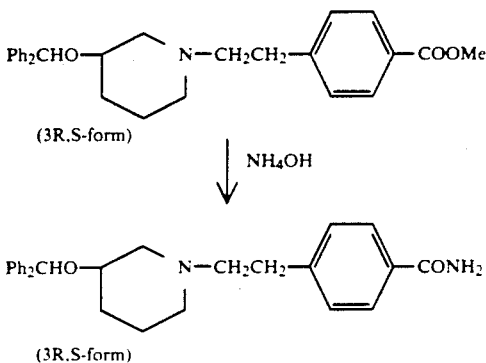

A mixture of (3R,S)-diphenylmethoxy-1-(4-methoxycarbonylphenethyl)piperidine (0.43 g) (see Example 17) and 0.880 aqueous ammonia solution (5 ml) in tetrahydrofuran (5 ml) was heated in a steel bomb at 80° for nineteen hours and then evaporated. The residue was partitioned between ethyl acetate and water and the organic layer was washed with water, dried over magnesium sulphate and evaporated. The residue was separated by chromatography on silica (8 g) using methylene chloride:ethyl acetate (4:1) plus 1–20% methanol as the eluant. Appropriate fractions were combined and evaporated to give the title compound as a colourless solid which was characterised as a hemihydrate (150 mg, 37%), m.p. 165°–166°.

Analysis %: Found: C, 76.7; H, 7.1; N, 6.6; $C_{27}H_{30}N_2O_2$; $0.5H_2O$ requires: C, 76.6; H, 7.4; N, 6.6.

EXAMPLE 66

(3R)-Diphenylmethoxy-1-[4-(N-methylcarbamoyl)phenethyl]piperidine

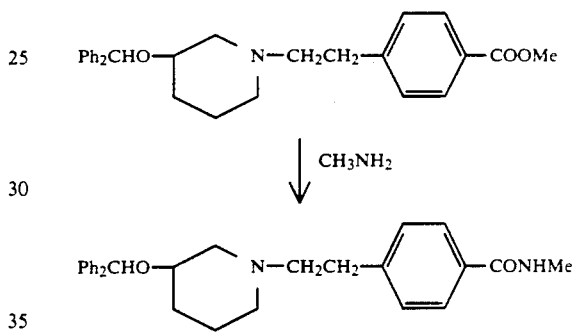

This was obtained as described in Example 64 using 33% ethanolic methylamine solution instead of 0.880 aqueous ammonia solution. The title compound was obtained as a colourless oil (327 mg, 97%), $[\alpha]_D^{25}$ +24.9° (c 1.005 in methanol).

Analysis %: Found: C, 78.5; H, 7.4; N, 6.4; $C_{28}H_{32}N_2O_2$ requires: C, 78.5; H, 7.5; N, 6.5.

EXAMPLE 67

1-(3-Carbamoylphenethyl)-(3R,S)-diphenylmethoxypiperidine

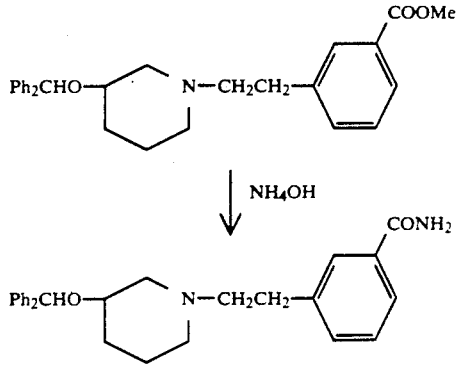

This was prepared as described in Example 64 but using (3R,S)-diphenylmethoxy-1-(3-methoxycarbonylphenethyl)piperidine (see Example 87) instead of (3R)-diphenylmethoxy-1-(4-methoxycarbonylphenethyl)- piperidine. The title compound was obtained as a colourless oil (27 mg, 23%).

Analysis %: Found: C, 78.4; H, 7.3; N, 6.5; C$_{27}$H$_{30}$N$_2$O$_2$ requires: C, 78.2; H, 7.3; N, 6.8.

EXAMPLE 68

1-(3-Carbamoylphenethyl)-(3R)-diphenylmethoxypiperidine

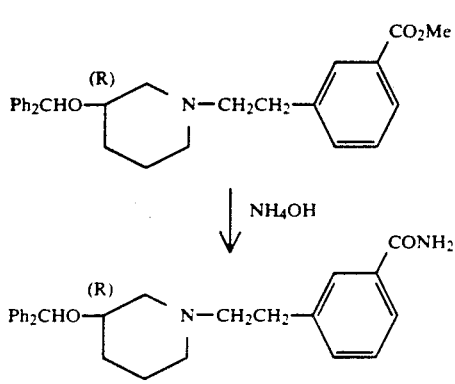

This was prepared as described in Example 64 using (3R)-diphenylmethoxy-1-(3-methoxycarbonylphenethyl)piperidine (see Example 88) instead of (3R)-diphenylmethoxy-1-(4-methoxycarbonylphenethyl)piperidine. The title compound was obtained as a colourless oil, (0.12 g, 24%).

Analysis %: Found: C, 74.4; H, 7.2; N, 5.6; C$_{27}$H$_{30}$N$_2$O$_2$.H$_2$O requires: C, 75.0; H, 7.4; N, 6.5.

EXAMPLE 69

(3R,S)-Diphenymethoxy-1-[3-(N-methylcarbamoyl)phenethyl]piperidine

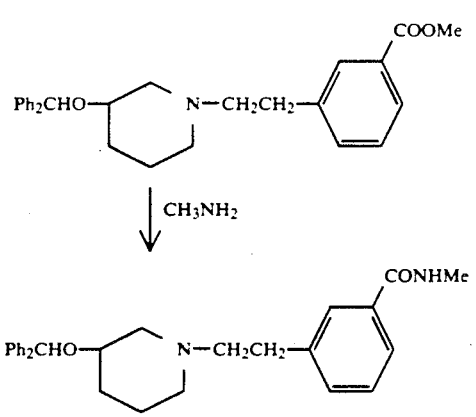

This was prepared as described in Example 64 from (3R.S)-diphenylmethoxy-1-(3-methoxycarbonylphenethyl)piperidine (see Example 87) and 33% methylamine in ethanol solution. The title compound was obtained as a colourless oil (64 mg, 38%).

Analysis %: Found: C, 78.0; H, 7.7; N, 6.4; C$_{28}$H$_{32}$N$_2$O$_2$ requires: C, 78.5; H, 7.5; N, 6.5.

EXAMPLE 70

1-(3-Aminophenethyl)-(3R,S)-diphenylmethoxypiperidine

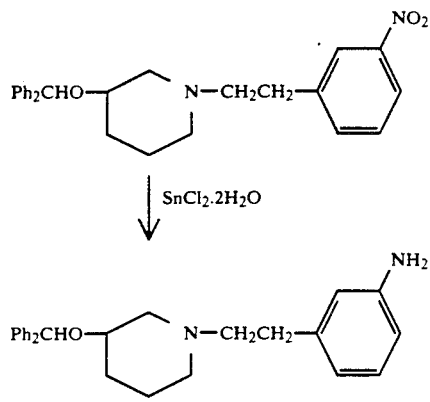

A mixture of (3R,S)-diphenylmethoxy-1-(3-nitrophenethyl)piperidine (4.1 g) (see Example 12) and stannous chloride dihydrate (10.8 g) in ethanol (50 ml) was heated under reflux for one hour, diluted with ethyl acetate and saturated aqueous sodium hydrogen carbonate, and the layers were separated. The organic layer was washed with water, dried over sodium sulphate and evaporated. The residue was purified by chromatography on silica (25 g) using methylene chloride plus 0-2% methanol as the eluant. Appropriate fractions were combined and evaporated to give the title compound as an oil (3.26 g, 93%).

Analysis 5: Found: C, 80.8; H, 7.8; N, 7.2; C$_{26}$H$_{30}$N$_2$O requires: C, 80.8; H, 7.8; N, 7.2.

EXAMPLE 71-74

The following compounds (R,S-forms) were prepared by reduction of the appropriate nitro-substituted starting materials (R,S-forms) (see Examples 13, 19, 11 and 24 respectively) with stannous chloride dihydrate as described in Example 70.

Example 72 was characterised by $^1$H-n.m.r. (CDCl$_3$): δ=7.20–7.50 (10H, m); 6.48–6.66 (3H, m); 5.59 (1H, s); 3.55–3.70 (3H, m); 3.12 (2H, d, J=6 Hz); 2.51–2.87 (5H, m) and 1.24–2.15 (6H, m).

In example 71, a solution of ether saturated with hydrogen chloride was added to a solution of the crude free base in ether. The mixture was kept at room temperature for 16 hours and the supernatant was decanted from the precipitated oil. This oil was dried to give the hydrochloride salt as a colourless foam.

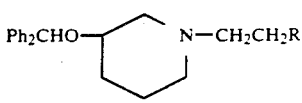

| Example | R | Form Characterised | Analysis % (Theoretical in brackets) | | |
|---|---|---|---|---|---|
| | | | C | H | N |
| 71 | 4-methyl-aminophenyl (para-NH₂, meta-Me) | Hydrochloride, foam | 73.6 (73.8 | 7.5 7.4 | 6.4 6.6) |
| 72 | 2-hydroxy-4-methyl-aminophenyl | Free base, oil | Characterised by $^1$H-n.m.r. (vide infra) | | |
| 73 | 2-methoxy-4-methyl-aminophenyl | Free base, oil | 77.2 (77.8 | 7.8 7.7 | 6.6 6.7) |
| 74 | 2-methylphenyl-NH₂ | Free base, oil | 80.5 (80.8 | 7.8 7.8 | 7.2 7.2) |

EXAMPLE 75

(3R,S)-Diphenylmethoxy-1-(4-methanesulphonamido-phenethyl)piperidine

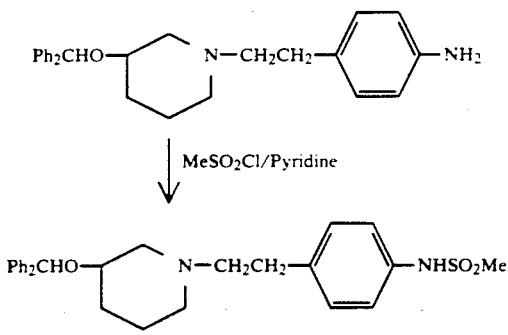

Methanesulphonyl chloride (0.165 g) was added dropwise to a stirred solution of 1-(4-aminophenethyl)-(3R,S)-diphenylmethoxypiperidine (0.50 g) (see Example 71) in pyridine (5 ml) and the mixture was stirred at room temperature for sixteen hours and then evaporated. The residue was partitioned between methylene chloride and saturated aqueous sodium hydrogen carbonate solution and the organic layer was washed with water, dried over sodium sulphate and evaporated. The residue was purified by chromatography on silica (8 g) using methylene chloride plus 0-1% methanol as the eluant. Appropriate fractions were combined and evaporated to give the title compound as a colourless oil (0.32 g, 53%).

Analysis %: Found: C, 69.7; H, 6.9; N, 6.0; C₂₇H₃₂N₂O₃S requires: C, 69.8; H, 6.9; N, 6.0.

EXAMPLE 76

(3R,S)-Diphenylmethoxy-1-(3-methanesulphonamido-phenethyl)piperidine

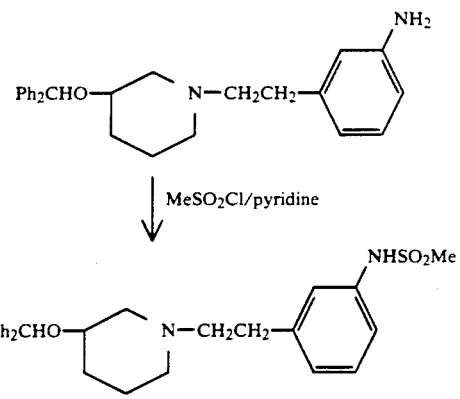

This was prepared as described in Example 75 using 1-(3-aminophenethyl)-(3R,S)-diphenylmethoxypiperidine (see Example 70) instead of 1-(4-aminophenethyl)-(3R,S)-diphenylmethoxypiperidine. The title compound was obtained as a colourless oil (0.21 g, 35%).

Analysis %: Found: C, 69.9; H, 7.1; N, 6.2; C₂₇H₃₂N₂O₃S requires: C, 69.8; H, 6.9; N, 6.0.

EXAMPLE 77

(3R,S)-Diphenylmethoxy-1-(4-ethanesulphonamido-phenethyl)piperidine

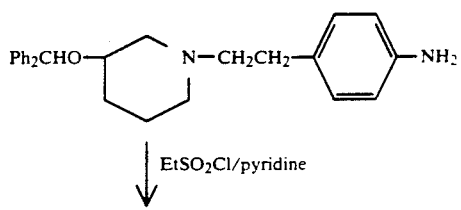

-continued

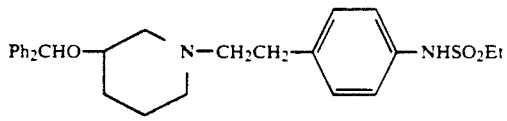

This was prepared as described in Example 75 using ethanesulphonyl chloride instead of methanesulphonyl chloride. The title compound was obtained as a pale yellow oil (0.40 g, 67%).

Analysis %: Found: C, 70.0; H, 7.4; N, 5.8; $C_{28}H_{34}N_2O_3S$ requires: C, 70.3; H, 7.2; N, 5.8.

EXAMPLE 78

1-(4-Acetamidophenethyl)-(3R,S)-diphenylmethoxypiperidine

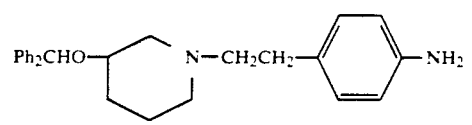

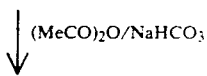

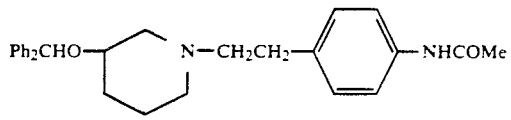

Acetic anhydride (154 mg) was added to a mixture of 1-(4-aminophenethyl)-(3R,S)-diphenylmethoxypiperidine (0.50 g) (see Example 71), sodium hydrogen carbonate (1.0 g), ethyl acetate (5 ml) and water (5 ml) and the mixture was shaken vigorously for twenty seconds and then allowed to stand at room temperature for ten minutes. The layers were separated and the organic layer was washed with saturated brine, dried over sodium sulphate and evaporated. The residue was purified by chromatography on silica (8 g) using methylene chloride plus 0-5% methanol as the eluant. Appropriate fractions were combined and evaporated to give the title compound as a colourless oil (0.33 g, 60%).

Analysis %: Found: C, 78.8; H, 7.7; N, 6.8; $C_{28}H_{32}N_2O_2$ requires: C, 78.5; H, 7.5; N, 6.5.

EXAMPLE 79

1-(3-Acetamidophenethyl)-(3R,S)-diphenylmethoxypiperidine

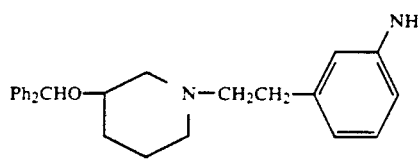

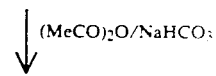

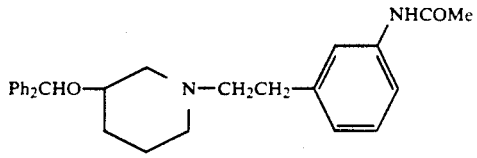

This was prepared as described in Example 78 using 1-(3-aminophenethyl)-(3R,S)-diphenylmethoxypiperidine (see Example 70) instead of 1-(4-aminophenethyl)-(3R,S)-diphenylmethoxypiperidine. The title compound was obtained as a pale yellow oil which was characterised with 0.25 molar equivalents of water (0.35 g, 63%).

Analysis %: Found: C, 77.8; H, 7.6; N, 6.6; $C_{28}H_{32}N_2O_2$; 0.25$H_2O$: C, 77.6; H, 7.6; N, 6.5.

EXAMPLE 80

1-(4-Acetamidomethylphenethyl)-(3R)-diphenylmethoxypiperidine

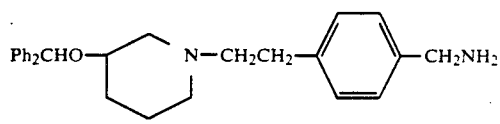

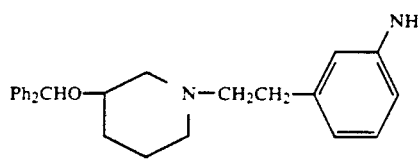

A mixture of acetic anhydride (115 mg) and 1-(4-aminomethylphenethyl)-(3R)-diphenylmethoxypiperidine (407 mg) (see Example 89) in methylene chloride (35 ml) was stirred at room temperature for 18 hours, washed with saturated aqueous sodium hydrogen carbonate solution, dried over magnesium sulphate and evaporated. The residue was purified by chromatography on silica (10 g) using methylene chloride plus 0-5% methanol as the eluant. Appropriate fractions were combined and evaporated to give the compound as a yellow oil which was characterised as a hemihydrate (349 mg, 76%), $[\alpha]_D^{25}$ +20.6° (c 0.925 in methanol).

Analysis %: found: C, 76.8; H, 8.0; N, 5.9; $C_{29}H_{34}N_2O_2$; 0.5$H_2O$ requires: C, 77.1; H, 7.8; N, 6.2.

EXAMPLE 81

(3R,S)-Diphenylmethoxy-1-(4-sulphamoylaminophenethyl)piperidine

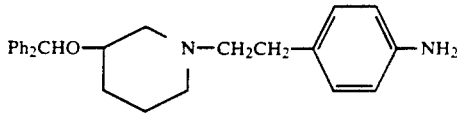

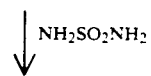

-continued

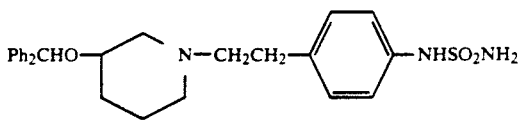

A solution of 1-(4-aminophenethyl)-(3R,S)-diphenylmethoxypiperidine (0.45 g) (see Example 71) and sulphamide (1.0 g) in dioxan (10 ml) was heated under reflux for one hour and evaporated. The residue was partitioned between ethyl acetate and water and the organic layer was dried over sodium sulphate and evaporated. The residue was purified by chromatography on silica (13 g) using methylene chloride plus 0–5% methanol as the eluant. Appropriate fractions were combined and evaporated to give the title compound as a colourless glass (0.24 g, 44%).

Analysis %: Found: C, 66.7; H, 6.8; N, 8.8; $C_{26}H_{31}N_3O_3S$ requires: C, 67.1; H, 6.7; N, 9.0.

EXAMPLE 82

(3R,S)-Diphenylmethoxy-1-(3-ethoxyphenethyl)piperidine

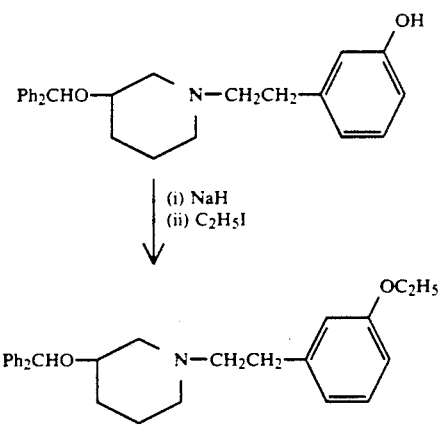

Sodium hydride (64 mg; 50% suspension in oil) was added to a solution of (3R,S)-diphenylmethoxy-1-(3-hydroxyphenethyl)piperidine (0.46 g) (see Example 15) in dimethylformamide (10 ml) and the mixture was stirred at room temperature for 30 minutes, treated with iodoethane (0.19 g) and then stirred at room temperature for three hours. The mixture was partitioned between ethyl acetate and water and the organic layer was washed with water, dried over sodium sulphate and evaporated. The residue was purified by chromatography on silica (9 g) using methylene chloride plus 0–1% methanol as the eluant. Appropriate fractions were combined and evaporated to give the title compound as a pale yellow oil (0.38 g, 77%).

Analysis %: Found: C, 80.9; H, 8.1; N, 3.3; $C_{28}H_{33}NO_2$ requires: C, 80.9; H, 8.0; N, 3.4.

EXAMPLE 83

(3R)-Diphenylmethoxy-1-[4-(N-methylcarbamoyloxy)-phenethyl]piperidine

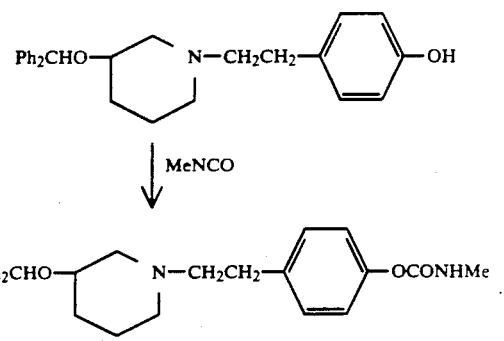

Methyl isocyanate (1.0 ml) was added to a solution of (3R)-diphenylmethoxy-1-(4-hydroxyphenethyl)piperidine (0.50 g) (see Example 35) in methylene chloride (25 ml) and the mixture was stirred at room temperature for sixty five hours and then evaporated. The residue was purified by chromatography on silica (4 g) using methylene chloride plus 0–2% methanol as the eluant. Appropriate fractions were combined and evaporated to give the title compound as a colourless oil, which was characterised as a hemihydrate (401 mg, 70%).

Analysis %: Found: C, 74.0; H, 7.7; N, 6.5; $C_{28}H_{32}N_2O_3$; $0.5H_2O$ requires: C, 74.1; H, 7.3; N, 6.2.

EXAMPLE 84

1-[2-(5-Carbamoyl-2-thienyl)ethyl]-(3R,S)-diphenylmethoxypiperidine

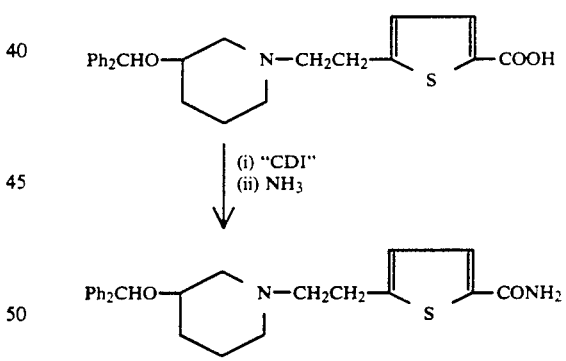

A mixture of 1-[2-(5-carboxy-2-thienyl)ethyl]-(3R,S)-diphenylmethoxypiperidine (126 mg) (see Preparation 17), and 1,1'-carbonyldiimidazole ("CDI") (49 mg) in tetrahydrofuran (20 ml) was stirred at room temperature for four hours and then treated with a saturated solution of ammonia in tetrahydrofuran (10 ml). The mixture was stirred at room temperature for twenty two hours and evaporated. The residue was partitioned between ethyl acetate and water and the organic layer was washed with water, dried over magnesium sulphate and evaporated. The residue was purified by chromatography on silica (7 g) using methylene chloride plus 0–20% methanol as the eluant. Appropriate fractions were combined and evaporated to give the title compound as a colourless gum (50 mg, 40%).

Analysis %: Found: C, 71.6; H, 6.7; N, 7.0; C25H28N2O2S requires: C, 71.4; H, 6.7; N, 6.7.

EXAMPLE 85

(3R)-Diphenylmethoxy-1-(4-methylaminomethyl-phenethyl)piperidine

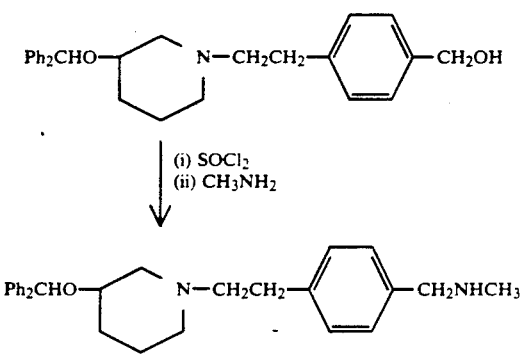

A solution of thionyl chloride (0.2 ml) and (3R)-diphenylmethoxy-1-(4-hydroxymethylphenethyl)-piperidine (300 mg) (see Example 61) in methylene chloride (25 ml) was heated under reflux for 2 hours and evaporated. The residue was azeotroped three times with n-hexane, treated with 33% methylamine in ethanol (25 ml), stirred at room temperature for sixteen hours and evaporated. The residue was partitioned between methylene chloride and 10% aqueous sodium carbonate solution and the organic layer washed with 10% aqueous sodium carbonate solution and saturated brine, dried over magnesium sulphate and evaporated. The residue was purified by chromatography on silica (10 g) using methylene chloride plus 0–10% methanol as the eluant. Appropriate fractions were combined and evaporated to give the title compound as a yellow oil (55 mg, 18%), $[\alpha]_D^{25}$ +20.0° (c 0.52 in methanol).

Analysis %: Found: C, 80.8; H, 8.3; N, 7.0; C28H34N2O requires: C, 81.1; H, 8.3; N, 6.8.

EXAMPLE 86

(3R)-Diphenylmethoxy-1-(2-hydroxyprop-2-ylphenethyl)piperidine

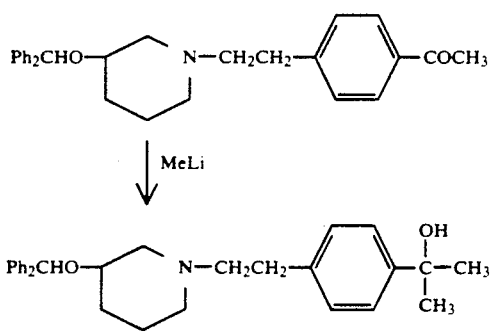

A 1.4M solution of methyllithium in hexane (0.90 ml) was added dropwise over five minutes to a stirred, ice-cooled solution of 1-(4-acetylphenethyl)-(3R)-diphenylmethoxypiperidine (0.50 g) (see Example 42) in ether (5 ml) and the mixture was stirred at room temperature for four hours, quenched with water and diluted with ether. The layers were separated and the organic layer was dried over magnesium sulphate and evaporated. The residue was purified by chromatography on silica (10 g) using methylene chloride plus 0–4% methanol as the eluant. Appropriate fractions were combined and evaporated to give, after recrystallisation from n-hexane, the title compound as a colourless solid, which was characterised as a hemihydrate (21 mg, 4%), m.p. 83°–85°.

Analysis %: Found: C, 79.6; H, 8.3; N, 3.3; C29H35NO2; 0.5H2O requires: C, 79.4; H, 8.3; N, 3.2.

EXAMPLE 87

(3R,S)-Diphenylmethoxy-1-(3-methoxycarbonylphenethyl)piperidine

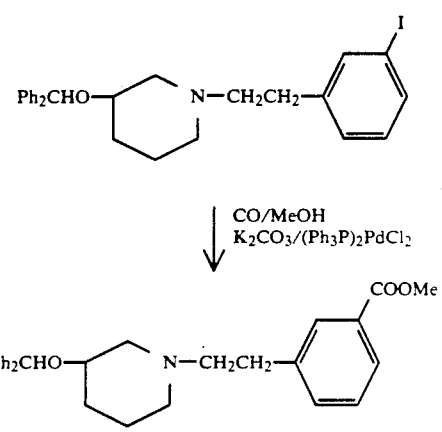

Carbon monoxide was bubbled through a stirred solution of (3R,S)-diphenylmethoxy-1-(3-iodophenethyl)piperidine (1.00 g) (see Example 23) in methanol (35 ml) to which was then added potassium carbonate (0.70 g) and bis(triphenylphosphine)palladium (II) chloride (30 mg). The mixture was stirred at room temperature for three hours with the continuous passage of carbon monoxide, filtered and evaporated. The residue was partitioned between ethyl acetate and saturated aqueous sodium hydrogen carbonate solution and the organic layer was dried over magnesium sulphate and evaporated. The residue was purified by chromatography on silica (15 g) using methylene chloride plus 0–2% methanol as the eluant. Appropriate fractions were combined and evaporated to give the title compound as a pale yellow oil (0.31 g, 36%) which was characterised by $^1$H-n.m.r.; (CDCl3); δ=7.91 (2H, s); 7.20–7.46 (12H, m); 5.59 (1H, s); 3.97 (3H, s); 3.52–3.63 (1H, m); 3.14 (1H, dd, J=6 and 2 Hz); 2.54–2.90 (5H, m) and 1.28–2.20 (6H, m).

EXAMPLE 88

(3R)-Diphenylmethoxy-1-(3-methoxycarbonylphenethyl)piperidine

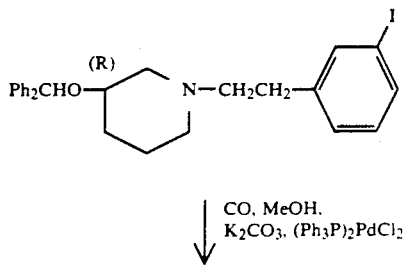

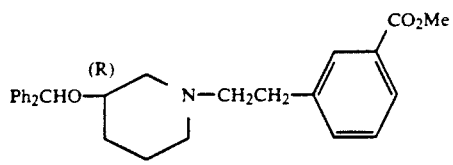

This was prepared as described in Example 87 using (3R)-diphenylmethoxy-1,3-iodophenethyl)piperidine (see Example 52) instead of (3R,S)-diphenylmethoxy-1-(3-iodophenethyl)piperidine. The title compound was obtained as a colourless oil, (0.52 g, 60%), which was characterised by $^1$H-n.m.r.

$^1$H-n.m.r. (CDCl$_3$) δ = 7.91 (2H, s); 7.20–7.55 (12H, m); 5.60 (1H, s); 3.97 (3H, s); 3.52–3.64 (1H, m); 3.13 (1H, dd, J = 7 and 2 Hz); and 1.25–2.90 (11H, m) ppm.

EXAMPLE 89

1-(4-Aminomethylphenethyl)-(3R)-diphenylmethoxypiperidine

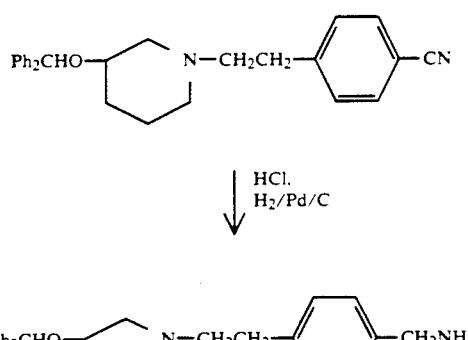

A solution of 1-(4-cyanophenethyl)-(3R)-diphenylmethoxypiperidine (3.18 g) (see Example 43) and concentrated hydrochloric acid (3.0 ml) in ethanol (155 ml) was stirred under 45 p.s.i. (310.3 kPa) of hydrogen in the presence of 10% palladium on charcoal (0.40 g) for 44 hours, filtered and evaporated. The residue was partitioned between methylene chloride and saturated aqueous sodium hydrogen carbonate solution and the organic layer was washed with water, dried over magnesium sulphate and evaporated. The residue was purified by chromatography on silica (50 g) using methylene chloride plus 0–15% methanol as the eluant. Appropriate fractions were combined and evaporated to give the title compound as a colourless oil (2.14 g, 60%).

Analysis 5%: Found: C, 79.5; H, 8.1; N, 6.5; C$_{27}$H$_{32}$N$_2$O requires: C, 79.2; H, 8.1; N, 6.8.

EXAMPLE 90

(3R)-Diphenylmethoxy-1-[4-(3-methylureidomethyl)-phenethyl]piperidine

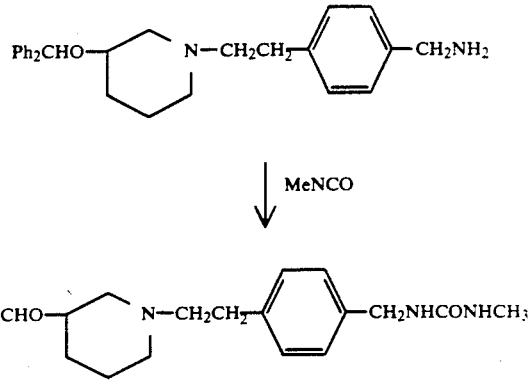

Methyl isocyanate (63 mg) was added to a solution of 1-(4-aminomethylphenethyl)-(3R)-diphenylmethoxypiperidine (400 mg) (see Example 89) in methylene chloride (30 ml) and the mixture was stirred at room temperature for 19 hours and evaporated. The residue was purified by chromatography on silica (10 g) using methylene chloride plus 0–10% methanol as the eluant. Appropriate fractions were combined and evaporated to give the title compound as a colourless oil (320 mg, 70%), $[α]_D^{25}$ +21.1° (c 0.835 in methanol).

Analysis %: Found: C, 75.8; H, 7.8; N, 9.4; C$_{29}$H$_{35}$N$_3$O$_2$ requires: C, 76.1; H, 7.7; N, 9.2.

EXAMPLE 91

(3R,S)-Diphenylmethoxy-1-(3,4-methylenedioxyphenethyl)piperidinium fumarate

A solution of fumaric acid (0.87 g) in warm ethanol (15 ml) was added to a solution of (3R,S)-diphenylmethoxy-1-(3,4-methylenedioxyphenethyl)piperidine (3.11 g) (see Example 1) and the mixture was stirred at room temperature for 64 hours. The resulting solid was collected, washed with ether and dried to give the title compound as a colourless solid (3.12 g, 78%), m.p. 171°–173°.

Analysis %: Found: C, 70.4; H, 6.4; N, 2.6; C$_{27}$H$_{29}$NO$_3$·C$_4$H$_4$O$_4$: C, 70.1; H, 6.2; N, 2.6.

EXAMPLE 92

(3R)-Diphenylmethoxy-1-(3,4-methylenedioxyphenethyl)piperidinium fumarate

The title compound was prepared as described in Example 91 using (3R)-diphenylmethoxy-1-(3,4-methylenedioxyphenethyl)piperidine (see Example 32) instead of (3R,S)-diphenylmethoxy-1-(3,4-methylenedioxyphenethyl)piperidine. The title compound was obtained as a colourless solid (0.53 g, 75%), m.p. 167°–169°.

Analysis %: Found: C, 70.0; H, 6.3; N, 2.5; C$_{27}$H$_{29}$NO$_3$·C$_4$H$_4$O$_4$ requires: C, 70.1; H, 6.2; N, 2.6.

EXAMPLE 93

(3R,S)-Diphenylmethoxy-1-(3-methoxyphenethyl)-piperidinium fumarate

The title compound was prepared as described in Example 91 using (3R,S)-diphenylmethoxy-1-(3- methoxyphenethyl)piperidine (see Example 8) instead of (3R,S)-diphenylmethoxy-1-(3,4-methylenedioxyphenethyl)piperidine. The title compound was obtained as a colourless solid (1.80 g, 50%), m.p. 148°-150°.

Analysis %: Found: C, 71.6; H, 6.7; N, 2.7; C27H31NO2.C4H4O4 requires: C, 71.9; H, 6.8; N, 2.7.

EXAMPLE 94

1-[2-(Benzodioxan-6-yl)ethyl]-(3R,S)-diphenylmethoxypiperidinium fumarate

The title compound was prepared as described in Example 91 using 1-[2-(benzodioxan-6-yl)ethyl]-(3R,S)-diphenylmethoxypiperidine (see Example 2) instead of (3R,S)-diphenylmethoxy-1-(3,4-methylenedioxyphenethyl)piperidine. The title compound was obtained as a colourless solid (2.53 g, 60%), m.p. 213°-214°.

Analysis %: Found: C, 70.3; H, 6.5; N, 2.6; C28H31NO3.C4H4O4 requires: C, 70.4; H, 6.5; N, 2.6.

EXAMPLE 95

(3R,S)-Diphenylmethoxy-1-(2-hydroxyphenethyl)-piperidine

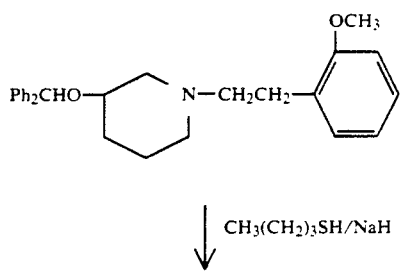

Sodium hydride (0.16 g; 60% dispersion in oil) was added to a solution of butanethiol (0.31 g) in dimethylformamide (15 ml) and the mixture was stirred at room temperature for 2 hours, treated with a solution of (3R,S)-diphenylmethoxy-1-(2-methoxyphenethyl)-piperidine (0.50 g) (see Example 25) in dimethylformamide (5 ml), and heated under reflux for 3.5 hours. The mixture was then partitioned between water and ethyl acetate and the organic layer was washed with water, dried over sodium sulphate and evaporated. The residue was purified by chromatography on silica (5 g) using methylene chloride plus 0-2% methanol as the eluant. Appropriate fractions were combined and evaporated to give the title compound as a colourless oil (0.21 g).

Analysis %: Found: C, 80.4; H, 7.6; N, 3.3; C26H29NO2 requires: C, 80.6; H, 7.5; N, 3.6.

The following Preparations illustrate the preparation of the novel starting materials used in the previous Examples. All temperatures are in °C.:

PREPARATION 1

(3R,S)-Diphenylmethoxypiperidine

Method A

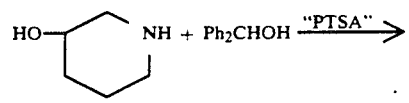

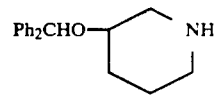

A solution of (3R,S)-hydroxypiperidine (50.5 g), benzhydrol (92.0 g) and para-toluenesulphonic acid monohydrate ("PTSA") (114.0 g) in toluene (600 ml) was heated under reflux for four hours using a Dean-Stark apparatus to remove the water formed. The mixture was then partitioned between 2M aqueous sodium hydroxide solution and ethyl acetate and the organic layer was washed with water and evaporated. The residue was partitioned between ether and 10% aqueous citric acid and the acidic layer was washed with ether, basified with excess solid sodium carbonate and extracted into ether. The organic layer was washed with water, dried over magnesium sulphate and evaporated to give the title compound as a colourless oil (89.2 g, 67%) which was characterised by its $^1$H-n.m.r. spectrum; (CDCl3): δ=7.22-7.45 (10H, m); 5.59 (1H, s); 3.38-3.48 (1H, m); 3.07 (1H, dd, J=6 and 2 Hz); 2.40-2.88 (3H, m) and 1.30-2.05 (5H, m).

Method B

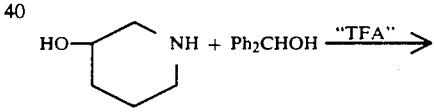

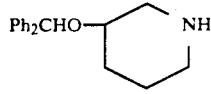

Trifluoroacetic acid ("TFA") (20 ml) was added cautiously to a stirred solution of (3R,S)-hydroxypiperidine (5.05 g) in methylene chloride (20 ml) and the mixture was treated portionwise with benzhydrol (9.20 g), stirred at room temperature for two hours and evaporated. The residue was dissolved in dioxan (50 ml), treated with 2M aqueous sodium hydroxide solution (50 ml), stirred at room temperature for two hours and partitioned between ether and water. The organic layer was washed with water, extracted into 2M hydrochloric acid, washed with ether, basified with excess solid sodium carbonate and extracted into ether. The organic layer was washed with water, dried over magnesium sulphate and evaporated to give the title compound as a colourless oil (5.30 g, 40%) whose spectral data was identical with that of the product obtained by Method A.

PREPARATION 2

(3R,S)-Di(4-fluorophenyl)methoxypiperidine

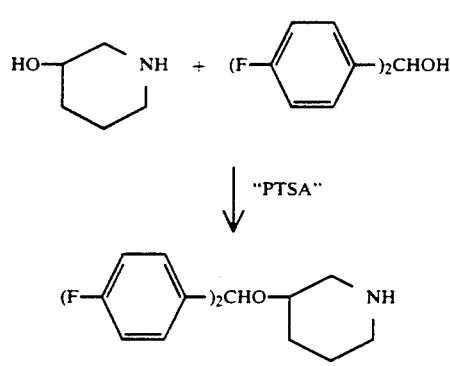

The title compound was prepared as described in Preparation 1, Method A using di(4-fluorophenyl)methanol (commercially available) instead of benzhydrol. The title compound was obtained as a colourless oil (4.01 g, 66%) which was characterised by its $^1$H-n.m.r. spectrum; (CDCl$_3$): δ=7.31 (4H, dt, J=8 and 10 Hz); 7.02 (4H, t, J=8 Hz); 5.50 (1H, s); 3.34–3.42 (1H, m); 3.08 (1H, dd, J=6 and 2 Hz); 2.60–2.89 (3H, m) and 1.32–2.00 (5H, m).

PREPARATION 3

(3R)-Di(4-fluorophenyl)methoxypiperidine

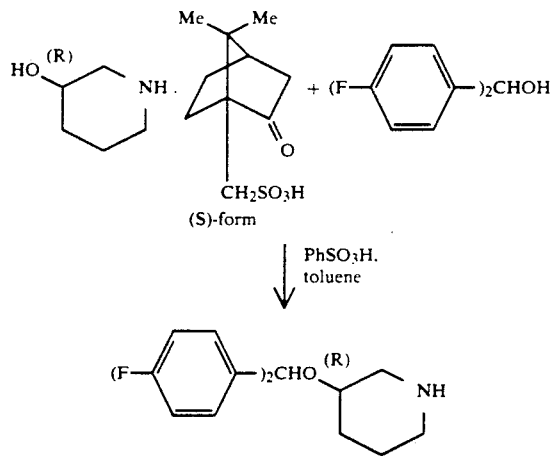

A mixture of di(4-fluorophenyl)methanol (2.20 g), (3R)-hydroxypiperidinium (1S)-camphor-10-sulphonate (see Preparation 7) (3.30 g) and benzenesulphonic acid (1.58 g) in toluene (60 ml) was heated under reflux in a Dean-Stark apparatus for 3 hours, washed with 10% aqueous sodium carbonate solution and evaporated. The residue was dissolved in ether and extracted with 10% aqueous citric acid solution. The acidic extract was washed with ether, basified with solid sodium carbonate and extracted with ether. The organic extract was washed with water, dried over MgSO$_4$ and evaporated to give the title compound as a colourless oil, (2.40 g, 79%).

Analysis %: Found: C, 71.7; H, 6.3; N, 4.7; C$_{18}$H$_{19}$F$_2$NO requires: C, 71.3; H, 6.3; N, 4.6.

PREPARATION 4

(3R)-[(R,S)-1-(2-Methylphenyl)-1-phenylmethoxy]-piperidine

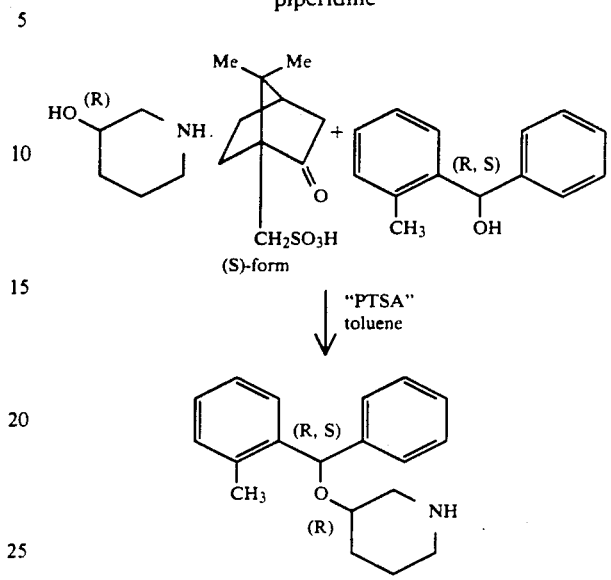

This was prepared as described in Preparation 3 using 1-(2-methylphenyl)-1-phenylmethanol and para-toluenesulphonic acid instead of di(4-fluorophenyl)methanol and benzenesulphonic acid. The title compound was obtained as a yellow oil, (5.76 g, 51%), which was used directly in Example 29 without further purification.

PREPARATION 5

(3R)-[(R,S)-1-(2-tert-Butylphenyl)-1-phenylmethoxy]-piperidine

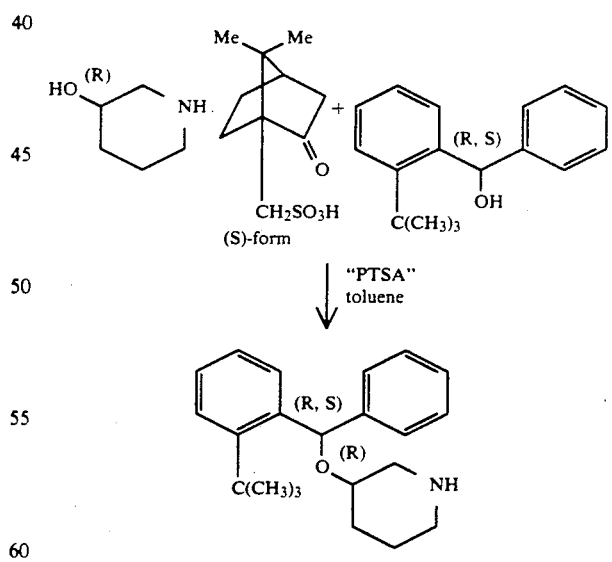

This was prepared as described in Preparation 3 using 1-(2-tert-butylphenyl)-1-phenylmethanol (see J. Med. Chem., 2, 57 (1960)) and para-toluenesulphonic acid instead of di(4-fluorophenyl)methanol and benzenesulphonic acid. The title compound was obtained as a colourless oil, (847 mg, 72%), which was used directly in Example 30 without further purification.

PREPARATION 6

(3R,S)-[(11H)-6,11-Dihydrodibenzo[b,e]thiepin-11-yloxy]piperidine

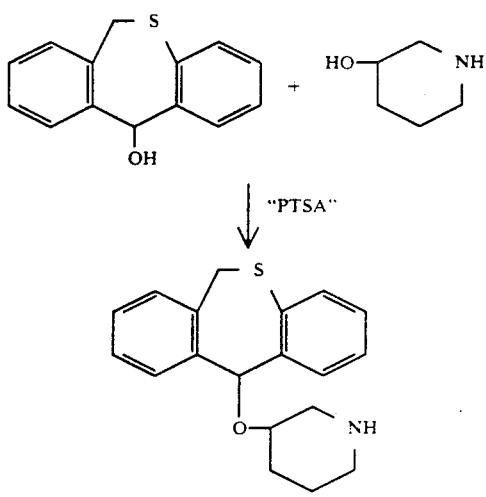

This was prepared as described in Preparation 1, Method A using (11H)-6,11-dihydrodibenzo[b,e]thiepin-11-ol (commercially available) instead of diphenylmethanol. The title compound was obtained as a pale orange oil (1.00 g, 12%) which was used directly in Example 31 without further purification or characterisation.

PREPARATION 7

(3R)-Diphenylmethoxypiperidine

This was prepared as described in Preparation 1, Method A using (3R)-hydroxypiperidinium (1S)-camphor-10-sulphonate [prepared by the method of B. Ringdahl, U. F. W. Ohnsorge and J. C. Craig, [J. Chem. Soc. Perkin II, (1981), 697] $[\alpha]_D^{25}$ +23.1° (c 1.5 in 50% aqueous ethanol)] instead of (3R,S)-hydroxypiperidine. The title compound was obtained as a colourless oil (2.7 g, 50%), $[\alpha]_D^{25}$ −3.3° (c 1.5 in ethanol).

Analysis %: Found: C, 80.2; H, 7.9; N, 5.1; $C_{18}H_{21}NO$ requires: C, 80.9; H, 7.9; N, 5.2.

PREPARATION 8

(3R,S)-Diphenylmethoxy-1-(3,4-methylenedioxyphenylacetyl)piperidine

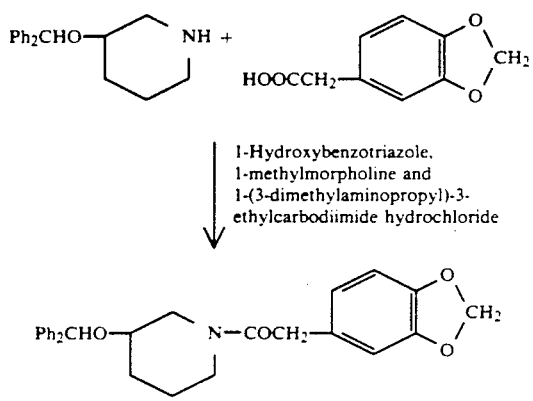

1-Methylmorpholine (1.50 g) was added to a mixture of (3R,S)-diphenylmethoxypiperidine (0.80 g) (see Preparation 1), 3,4-methylenedioxyphenylacetic acid (0.54 g), 1-hydroxybenzotriazole (0.51 g) and 1-(3-dimethylaminopropyl)-3-ethylcarbodiimide hydrochloride (1.20 g) in methylene chloride (50 ml) and the solution was stirred at room temperature for forty hours, washed successively with 2M hydrochloric acid, water, 10% aqueous sodium carbonate solution and water, dried over magnesium sulphate and evaporated to give the title compound as a colourless oil (1.19 g, 92%), which was characterised by its $^1$H-n.m.r. spectrum (CDCl$_3$): δ=7.2–7.5 (10H, m); 6.60–6.83 (3H, m); 5.98 (2H, s); 5.38 (s) and 5.64 (s) (1H); 3.20–3.95 (7H, m) and 1.25–2.00 (4H, m).

PREPARATIONS 9-14

The following compounds (R,S-forms) were prepared by the method described in Preparation 8 by coupling the appropriate arylacetic acid with (3R,S)-diphenylmethoxypiperidine (see Preparation 1). The arylacetic acids are in general known compounds. The starting material for Preparation 14 is described in Preparation 18.

The products from Preparations 12 and 13 were characterised by their $^1$H-n.m.r. spectra; Preparation 12 (CDCl$_3$): δ=7.2–7.6 (14H, m); 5.42 (s) and 5.63 (s) (1H); 3.30–3.92 (7H, m) and 1.25–2.00 (4H, m): Preparation 13 (CDCl$_3$): δ=7.22–7.50 (10H, m); 6.61–6.88 (3H, m); 5.36 (s) and 5.64 (s) (1H); 4.25 (4H, s); 3.16–4.02 (7H, m) and 1.23–2.00 (4H, m).

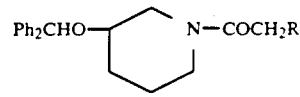

| Preparation | R | Analysis % (Theoretical in brackets) | | |
|---|---|---|---|---|
| | | C | H | N |
| 9 | ![meta-F-phenyl] | 77.2 (77.4 | 6.5 6.5 | 3.5 3.5) |
| 10 | ![benzofuran-like] | 78.3 (78.7 | 6.9 6.8 | 4.0 3.3) |
| 11 | ![3,4-diF-phenyl] | 74.1 (74.1 | 6.0 6.0 | 3.2 3.3) |
| 12 | ![meta-CF3-phenyl] | Characterised by $^1$H-n.m.r. (vide infra) | | |
| 13 | ![benzodioxan] | Characterised by $^1$H-n.m.r (vide infra) | | |

| Preparation | R | Analysis % (Theoretical in brackets) | | |
|---|---|---|---|---|
| | | C | H | N |
| 14 | 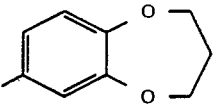 | 75.5 (76.1 | 6.9 6.8 | 3.0 3.0) |

PREPARATION 15

(3R)-Hydroxy-1-(4-methoxyphenethyl)piperidine

A mixture of (3R)-hydroxypiperidinium camphor-10-sulphonate (8.30 g) [prepared by the method of B. Ringdahl, U. F. W. Ohnsorge and J. C. Craig, J. Chem. Soc. Perkin II, (1981), 697] $[\alpha]_D^{25}$ +23.1° (c 1.5 in 50% aqueous ethanol)], 4-methoxyphenethyl bromide (5.4 g), sodium carbonate (5.30 g) and sodium iodide (250 mg) in acetonitrile (125 ml) was heated under reflux for 84 hours and evaporated. The residue was partitioned between methylene chloride and water and the organic layer was washed with saturated brine, dried over magnesium sulphate and evaporated. The residue was purified by chromatography on silica (60 g) using methylene chloride plus 0-3% methanol as the eluant. Appropriate fractions were combined and evaporated to give the title compound as a colourless oil (3.80 g, 65%), $[\alpha]_D^{25}$ +1.6° (c 1.0 in methanol), which was characterised by its $^1$H-n.m.r. spectrum: (CDCl$_3$): δ=7.15 (2H, d, J=8 Hz); 6.83 (2H, d, J=8 Hz); 3.80-3.88 (1H, m); 3.79 (3H, s); 2.32-2.80 (9H, m) and 1.48-1.92 (4H, m).

PREPARATION 16

(3R,S)-Hydroxy-1-(3-methoxyphenethyl)piperidine

This was prepared as described in Preparation 15 from (3R,S)-hydroxypiperidine and 3-methoxyphenethyl bromide. The title compound was obtained as a pale yellow oil (1.63 g, 72%) which was characterised by its $^1$H-n.m.r. spectrum; (CDCl$_3$): δ=7.21 (1H, dd, J=8 and 7 Hz); 6.72-6.83 (3H, m); 3.78-3.88 (1H, m); 3.81 (3H, s); 2.30-2.84 (9H, m) and 1.47-1.90 (4H, m).

PREPARATION 17

1-[2-(5-Carboxy-2-thienyl)ethyl]-(3R,S)-diphenylmethoxypiperidine

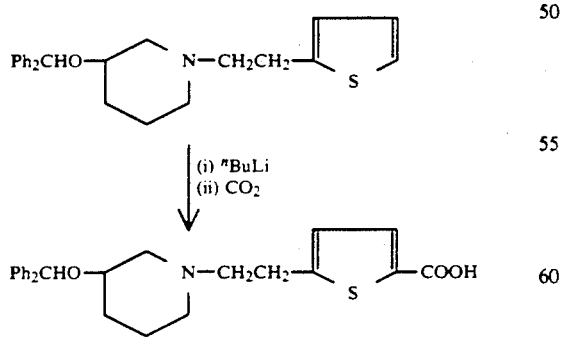

A 2.6M solution of n-butyllithium in hexane (1.28 ml) was added dropwise over ten minutes to a stirred solution of (3R,S)-diphenylmethoxy-1-[2-(2-thienyl)ethyl]-piperidine (378 mg) (see Example 21) in ether (25 ml) at −20° and the mixture was stirred at −20° for one hour and poured onto a mixture of solid carbon dioxide and ether. The mixture was diluted with water and the layers were separated. The aqueous layer was acidified with glacial acetic acid to pH 7 and extracted into ethyl acetate. The ethyl acetate extract was washed with water, dried over sodium sulphate and evaporated. The residue was purified by chromatography on silica (7 g) using methylene chloride plus 0-20% methanol as the eluant. Appropriate fractions were combined and evaporated to give the title compound as a colourless gum (70 mg, 17%).

Analysis %: Found: C, 70.9; H, 6.3; N, 3.3; C$_{25}$H$_{27}$NO$_3$S requires: C, 71.2; H, 6.5; N, 3.3.

PREPARATION 18

(Benzodioxepan-7-yl)acetic acid

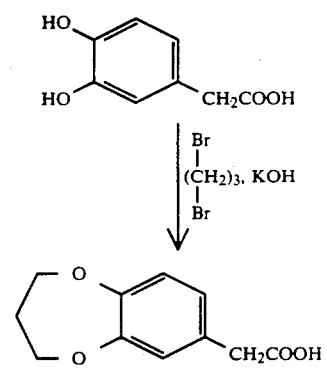

A mixture of 3,4-dihydroxyphenylacetic acid (5.0 g), 1,3-dibromopropane (7.2 g) and potassium hydroxide (7.3 g) in water (25 ml) was heated under reflux for 17 hours, acidified to pH 1 with 2M hydrochloric acid and extracted several times into methylene chloride. The combined organic extracts were dried over magnesium sulphate and evaporated. The residue was purified by chromatography on silica (75 g) using methylene chloride plus 0-2% acetic acid as the eluant. Appropriate fractions were combined and evaporated and the residue was taken up in methylene chloride and extracted into 5% aqueous sodium carbonate solution. The basic extract was washed with methylene chloride, acidified to pH 1 with 5M hydrochloric acid and extracted into methylene chloride. The organic extract was dried over magnesium sulphate and evaporated to give the title compound as a colourless solid (1.4 g, 23%), m.p. 99°-101°.

Analysis %: Found: C, 63.4; H, 5.9; N, 0.0; C$_{11}$H$_{12}$O$_4$ requires: C, 63.4; H, 5.8; N, 0.0.

PREPARATION 19

3,4-Methylenedioxyphenethyl alcohol

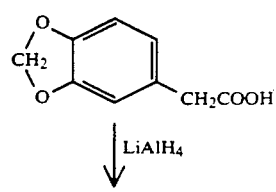

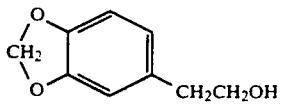

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%), which was characterised by its $^1$H-n.m.r. spectrum.

$^1$H-n.m.r. (CDCl$_3$) δ=6.69–6.83 (3H, m); 5.98 (2H, s); 3.82 (2H, dt, J=7 and 6 Hz); 2.81 (2H, t, J=7 Hz) and 1.44 (1H, t, J=6 Hz, exchangeable with D$_2$O).

PREPARATION 20

3,4-Methylenedioxyphenethyl bromide

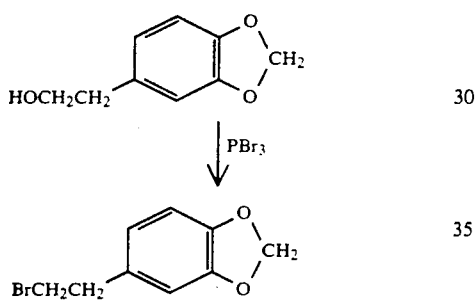

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 19) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g, 40%), which was characterised by its $^1$H-n.m.r. spectrum.

$^1$H-n.m.r. (CDCl$_3$) δ=6.80 (1H, d, J=8 Hz), 6.75 (1H, s); 6.71 (1H, d, J=8 Hz); 6.00 (2H, s); 3.56 (2H, t, J=7 Hz) and 3.13 (2H, t, J=7 Hz).

PREPARATION 21

3-Hydroxy-4-methoxyphenethyl chloride

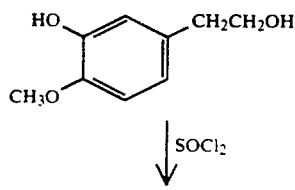

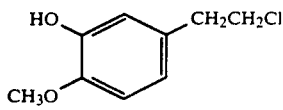

A mixture of 3-hydroxy-4-methoxyphenethyl alcohol (2.25 g) and thionyl chloride (5 ml) in methylene chloride (120 ml) was heated under reflux for 16 hours and evaporated. The residue was azeotroped twice with hexane and purified by chromatography on silica (30 g) using methylene chloride plus 0–6% methanol as the eluant. Appropriate fractions were combined and evaporated to give the title compound as a colourless solid (0.82 g, 33%), m.p. 53°–54°, which was characterised by its $^1$H-n.m.r. spectrum.

$^1$H-n.m.r. (CDCl$_3$) δ=6.86 (1H, d, J=8 Hz); 6.82 (1H, d, J=2 Hz); 6.73 (1H, dd, J=8 and 2 Hz); 5.61 (1H, s, exchangeable with D$_2$O); 3.92 (3H, s); 3.70 (2H, t, J=7 Hz) and 3.01 (2H, t, J=7 Hz).

PREPARATION 22

6-(2-Hydroxyethyl)benzodioxan

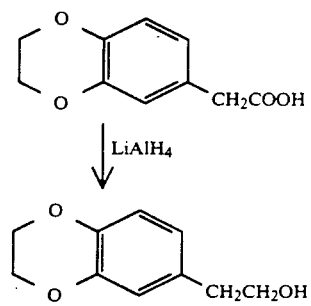

This was prepared as described in Preparation 19 using (benzodioxan-6-yl)acetic acid instead of 3,4-methylenedioxyphenylacetic acid. The title compound was obtained as a colourless oil (19.8 g, 92%), which was characterised by its $^1$H-n.m.r. spectrum.

$^1$H-n.m.r. (CDCl$_3$) δ=6.84 (1H, d, J=8 Hz); 6.77 (1H, d, J=2 Hz); 6.73 (1H, dd, J=8 and 2 Hz); 4.28 (4H, s); 3.59 (2H, t, J=7 Hz) and 3.08 (2H, t, J=7 Hz).

PREPARATION 23

6-(2-Bromoethyl)benzodioxan

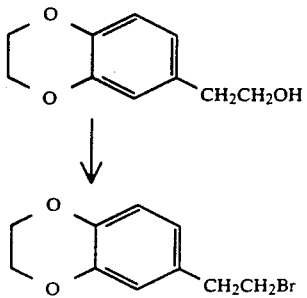

This was prepared as described in Preparation 20 using 6-(2-hydroxyethyl)benzodioxan (see Preparation 22) instead of 3,4-methylenedioxyphenethyl alcohol. The title compound was obtained as a pale yellow oil (21.4 g, 80%), which was characterised by its $^1$H-n.m.r. spectrum.

$^1$H-n.m.r. (CDCl$_3$) $\delta$=6.83 (1H, d, J=8 Hz); 6.77 (1H, d, J=2 Hz); 6.72 (1H, dd, J=8 and 2 Hz); 4.28 (4H, s); 3.59 (2H, t, J=7 Hz) and 3.10 (2H, t, J=7 Hz).

PREPARATION 24

4-Hydroxy-3-nitrophenethyl chloride

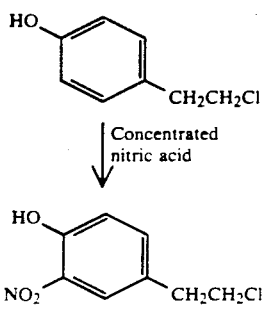

A solution of concentrated nitric acid (1.8 ml) in acetic acid (4 ml) was added to a stirred solution of 4-hydroxyphenethyl chloride (4.5 g) in acetic acid (25 ml), keeping the temperature below 15°. The mixture was then stirred at 10° for 3.5 hours, poured into water, and extracted into ethyl acetate. The organic extract was washed with 5% aqueous sodium carbonate solution, dried over magnesium sulphate and evaporated. The residue was purified by chromatography on silica (50 g) using hexane plus 0–10% ethyl acetate as the eluant. Appropriate fractions were combined and evaporated to give the title compound as a colourless solid (3.2 g, 55%), m.p. 53°–55°.

Analysis %: Found: C, 48.0; H, 3.7; N, 6.9; C$_8$H$_8$ClNO$_3$ requires: C, 47.6; H, 4.0; N, 6.9.

PREPARATION 25

4-Methoxy-3-nitrophenethyl chloride

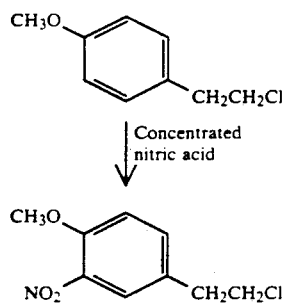

This was prepared as described in Preparation 24 using 4-methoxyphenethyl chloride instead of 4-hydroxyphenethyl chloride. The title compound was obtained as a pale yellow oil (1.9 g, 18%).

Analysis %: Found: C, 50.4; H, 4.6; N, 6.5; C$_9$H$_{10}$ClNO$_3$ requires: C, 50.1; H, 4.7; N, 6.5.

PREPARATION 26

3-Iodophenethyl alcohol

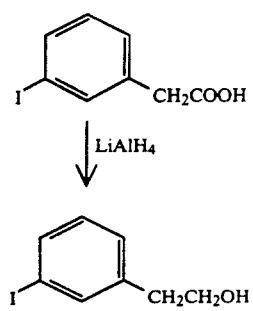

This was prepared as described in Preparation 19 using 3-iodophenylacetic acid (commercially available) instead of 3,4-methylenedioxyphenylacetic acid. The title compound was obtained as a colourless oil (2.2 g, 58%), which was characterised by its $^1$H-n.m.r. spectrum.

$^1$H-n.m.r. (CDCl$_3$) $\delta$=7.58-7.70 (2H, m); 7.23 (1H, d, J=8 Hz); 7.04 (1H, d, J=8 Hz); 3.91 (2H, t, J=7 Hz); 2.84 (2H, t, J=7 Hz) and 1.43 (1H, broad s, exchangeable with D$_2$O).

PREPARATION 27

3-Iodophenethyl bromide

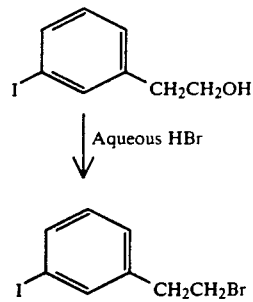

A mixture of 3-iodophenethyl alcohol (see Preparation 26) (1.2 g) and 48% aqueous hydrobromic acid (20 ml) was stirred at room temperature for 8 hours, poured into water and extracted into methylene chloride. The organic extracts were washed with saturated aqueous sodium hydrogen carbonate solution and water, dried over sodium sulphate and evaporated to give the title compound as a pale brown oil (1.1 g, 73%), which was characterised by its $^1$H-n.m.r. spectrum.

$^1$H-n.m.r. (CDCl$_3$) $\delta$=7.60-7.70 (2H, m); 7.22 (1H, d, J=8 Hz); 7.07 (1H, t, J=8 Hz); 3.58 (2H, t, J=7 Hz) and 3.16 (2H, t, J=7 Hz).

PREPARATION 28

N-[4-(2-methylsulphonyloxyethyl)phenyl]methanesulphonamide

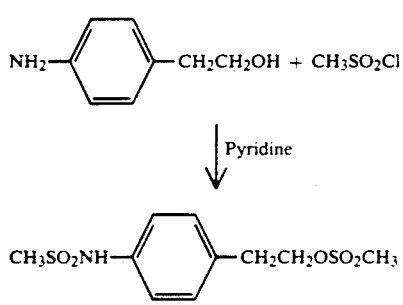

Methanesulphonyl chloride (50.4 g) was added dropwise to a stirred solution of 4-aminophenethyl alcohol (27.44 g) in dry pyridine (300 ml) at 0° C. and the solution was stirred at 0° C. for 30 minutes and then at room temperature for 2.5 hours. It was then poured into water and the solid was filtered off, washed with water, dried and crystallised from ethyl acetate to give the title compound (39.0 g, 66%), m.p. 136°–137° C.

Analysis %: Found: C, 40.6; H, 5.2; N, 4.9; $C_{10}H_{15}NO_5S_2$ requires: C, 40.9; H, 5.1; N, 4.8.

PREPARATION 29

5-(2-Bromoethyl)indane

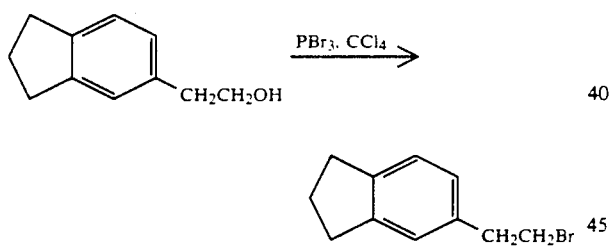

Phosphorous tribromide (3.5 ml) was added, dropwise, to an ice-cooled solution of 5-(2-hydroxyethyl)indane (prepared as described in FR-2,139,628) (14.0 g) in carbon tetrachloride (100 ml) and the mixture was heated under reflux for 2 hours, quenched with ice-water and partitioned between dichloromethane and 10% aqueous sodium carbonate solution. The organic layer was washed with water, dried over magnesium sulphate and evaporated under reduced pressure. The residue was purified by chromatography on silica gel using dichloromethane as eluant. Appropriate fractions were combined and evaporated under reduced pressure to give the title compound as a pale yellow oil, (10.5 g, 54%).

$^1$H-n.m.r. (300 MHz. CDCl$_3$) δ=7.20 (dd, 1H, J=8 and 1.5 Hz); 7.10 (d, 1H, J=1.5 Hz); 6.99 (d, 1H, J=8 Hz); 3.58 (t, 2H, J=7 Hz); 3.17 (t, 2H, J=7 Hz); 2.80–3.02 (m, 4H); and 2.02–2.18 (m, 2H) ppm.

PREPARATION 30

5-(2-Hydroxyethyl)-2,3-dihydrobenzofuran

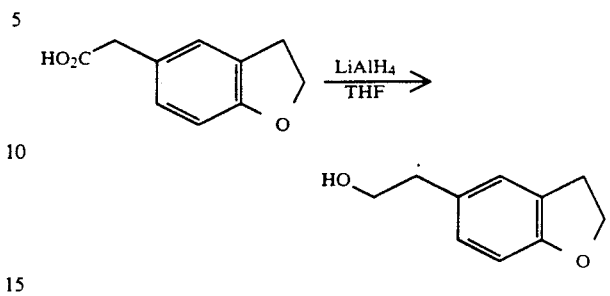

A solution of (2,3-dihydrobenzofuran-5-yl)acetic acid (4.9 g—see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as as oil, (3.3 g).

$^1$H-n.m.r. (CDCl$_3$) δ=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (broad s, 1H) ppm.

PREPARATION 31

5-(2-Bromoethyl)-2,3-dihydrobenzofuran

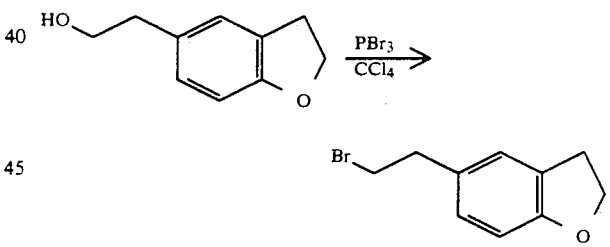

Phosphorus tribromide (0.37 g) was added to a solution of 5-(2-hydroxyethyl)-2,3-dihydrobenzofuran (0.612 g—see Preparation 30) in carbon tetrachloride (3 ml) and the mixture was heated under reflux for 3 hours. On cooling to room temperature, the mixture was partitioned between 10% aqueous sodium carbonate (20 ml) and dichloromethane (20 ml). The layers were separated and the aqueous layer was extracted with dichloromethane (2×10 ml). The combined dichloromethane extracts were dried (MgSO$_4$) and concentrated in vacuo to give the title compound as an oil which crystallised on standing, (0.584 g), m.p. 60°–62° C.

$^1$H-n.m.r. (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

We claim:

1. A compound having the (3R,S)- or (3R)-configuration of the formula:

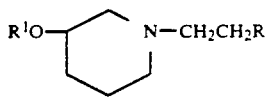

or a pharmaceutically acceptable acid addition salt thereof, wherein $R^1$ is a group of the formula:

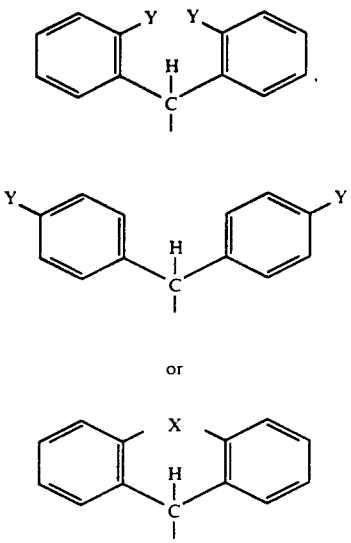

where each Y, which may be the same or different, is selected from hydrogen, halogen and $C_1$-$C_4$ alkyl; and X is —$(CH_2)_2$—, —CH=CH—, —$CH_2$—S—, —$CH_2O$—, —S— or —O—; and R is a group of the formula:

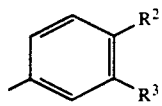

where $R^2$ and $R^3$, taken together, and attached to adjacent carbon atoms, represent a group of the formula —$O(CH_2)_mO$— where m is 1, 2 or 3, —$O(CH_2)_2$— or —$(CH_2)_3$—.

2. A compound as claimed in claim 1 wherein R is:

and $R^2$ and $R^3$ are as previously defined in claim 1.

3. A compound as claimed in claim 1 wherein $R^1$ is a group selected from the group consisting of diphenylmethyl, di(4-fluorophenyl)methyl, 1-(2-methylphenyl)-1-phenyl-methyl, 1-(2-tert-butylphenyl)-1-phenyl-methyl, (11H)-6,11-dihydrodibenzo[b,e]thiepin-11-yl, (5H)-dibenzo[a,d]cyclohepten-5-yl and (5H)-10,11-dihydrodibenzo[a,d]cyclohepten-5-yl.

4. A compound as claimed in claim 1 wherein $R^1$ is diphenylmethyl.

5. A compound as claimed in claim 1 wherein $R^2$ and $R^3$ represent —$O(CH_2)_mO$— where m is 1, whereby R is 3,4-methylenedioxyphenyl.

6. A compound as claimed in claim 1 wherein $R^1$ is diphenylmethyl and R is 3,4-methylenedioxyphenyl.

7. A compound as claimed in claim 1 which has the (3R,S)-configuration.

8. A compound as claimed in claim 1 which has the (3R)-configuration.

9. (3R)-Diphenylmethoxy-1-(3,4-methylenedioxyphenethyl)piperidine.

10. A pharmaceutical composition useful for treating diseases associated with altered motility or smooth muscle tone or both, said composition comprising a pharmaceutically acceptable carrier or diluent and an anticholinergically-effective amount of a compound as claimed in claim 1.

11. The composition according to claim 10 wherein the compound is (3R)-diphenylmethoxy-1-(3,4-methylenedioxyphenethyl)piperidine.

12. A method for treating diseases associated with altered motility or smooth muscle tone or both in a mammal in need of such treatment, which comprises administering to said subject an anti-cholinergically-effective amount of a compound as claimed in claim 1.

13. The method as claimed in claim 12 wherein said compound is (3R)-diphenylmethoxy-1-(3,4-methylenedioxyphenethyl)piperidine.

14. The method as claimed in claim 12 wherein said mammal in need of treatment is afflicted with a disease selected from the group consisting of irritable bowel syndrone, diverticular disease, urinary incontinence, oesophageal achalasia and chronic obstructive airways disease.

* * * * *